United States Patent
Wang et al.

(10) Patent No.: US 12,172,106 B2
(45) Date of Patent: Dec. 24, 2024

(54) METHODS FOR ASSESSING BINDING AFFINITY OF AN ANTIBODY VARIANT TO THE NEONATAL FC RECEPTOR

(71) Applicant: Regeneron Pharmaceuticals, Inc., Tarrytown, NY (US)

(72) Inventors: Hongxia Wang, Briarcliff Manor, NY (US); Haibo Qiu, Hartsdale, NY (US); Ning Li, New Canaan, CT (US); Xueqing Zhao, Mamaroneck, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 930 days.

(21) Appl. No.: 16/535,128

(22) Filed: Aug. 8, 2019

(65) Prior Publication Data

US 2020/0047085 A1 Feb. 13, 2020

Related U.S. Application Data

(60) Provisional application No. 62/716,835, filed on Aug. 9, 2018.

(51) Int. Cl.
  *B01D 15/38* (2006.01)
  *B01D 15/32* (2006.01)
  (Continued)

(52) U.S. Cl.
  CPC ....... *B01D 15/3809* (2013.01); *B01D 15/325* (2013.01); *B01D 15/426* (2013.01);
  (Continued)

(58) Field of Classification Search
  None
  See application file for complete search history.

(56) References Cited

U.S. PATENT DOCUMENTS

2004/0072251 A1* 4/2004 Anderson .......... G01N 33/6848
                                                      435/7.1
2009/0269338 A1    10/2009 Huang et al.
                       (Continued)

OTHER PUBLICATIONS

Zhang, C. et al. High performance affinity chromatography and related separation methods for the analysis of biological and pharmaceutical agents, Analyst, 2018, 143, 374-391 (Published on Year: 2017) (Year: 2017).*

Cymer et al., Evaluation of an FcRn affinity chromatographic method for IgG1-type antibodies and Evaluation of IgG variants. Bioanalysis. Sep. 2017; 9(17):1305-17.

(Continued)

*Primary Examiner* — Xiaoyun R Xu
(74) *Attorney, Agent, or Firm* — McCarter & English, LLP; Maria Laccotripe Zacharakis

(57) ABSTRACT

The present invention provides methods to quickly and efficiently assess the effect of antibody variants, including PTMs, e.g., glycosylation, oxidation, and deamidation variants, on the binding between the antibody and FcRn. In particular, the present invention is based, at least in part, on the development of an online, two dimension liquid chromatography (2D-LC) method for assessing binding between antibody variants and FcRn. In one aspect, the online 2D-LC is coupled with mass spectrometry (MS). The present invention allows for differentiation of antibody variants by peak pattern and retention time profile by affinity chromatography, and identification of these variants by mass spectrometry analysis.

23 Claims, 9 Drawing Sheets

(51) Int. Cl.
  B01D 15/42      (2006.01)
  G01N 30/72      (2006.01)
  G01N 33/557     (2006.01)
  G01N 33/68      (2006.01)
  G01N 30/02      (2006.01)

(52) U.S. Cl.
  CPC ....... *G01N 30/7233* (2013.01); *G01N 33/557* (2013.01); *G01N 33/6848* (2013.01); *G01N 33/6857* (2013.01); *G01N 2030/027* (2013.01)

(56) References Cited

U.S. PATENT DOCUMENTS

2014/0357843 A1   12/2014   Oh et al.
2017/0227547 A1    8/2017   Emrich et al.
2018/0127498 A1    5/2018   Bhatta et al.

OTHER PUBLICATIONS

Schlothauer et al., Analytical FcRn affinity chromatography for functional characterization of monoclonal antibodies. MAbs. Jul.-Aug. 2013; 5(4):576-86.

Stoll et al., Development of comprehensive online two-dimensional liquid chromatography/mass spectrometry using hydrophilic interaction and reversed-phase separations for rapid and deep profiling of therapeutic antibodies. Anal Chem. 2018; 90(9):5923-9.

Thermo Scientific. MAbPac RP Column. Thermofisher.com/biolc. Thermo Fisher Scientific Inc., 7 pages, (2016).

Wang et al., Purification and characterization of a single-chain chimeric anti-p185 antibody expressed by CHO-GS system. Protein Expr Purif. May 2005; 41(1):68-76.

Extended European Search Report and Written Opinion for Application No. EP19190825.0, dated Dec. 20, 2019, 11 pages.

* cited by examiner

Column 1: FcRn Affinity Column (Roche Diagnostics)
Flow Rate: 0.08 mL/min
Buffer A: 20 mM MES/HCl, pH 5.5, 140 mM NaCl
Buffer B: 20 mM Tris/HCl, pH 8.8, 140 mM NaCl

| Time (min) | % Buffer A | % Buffer B |
|---|---|---|
| 0 | 80 | 20 |
| 10 | 80 | 20 |
| 80 | 0 | 100 |
| 90 | 0 | 100 |
| 93 | 80 | 20 |
| 103 | 80 | 20 |

FIG. 2B

Column 2: MAbPac-RP, 2.1mm×50mm (Thermo Fisher Scientific)
Flow Rate: 0.3 mL/min
Buffer A: 0.1% formic acid in water
Buffer B: 0.1% formic acid in acetonitrile

| Time (min) | % Buffer A | % Buffer B |
|---|---|---|
| 0 | 99 | 1 |
| 5 | 99 | 1 |
| 9 | 55 | 45 |
| 9.5 | 10 | 90 |
| 11 | 10 | 90 |
| 11.1 | 99 | 1 |
| 17 | 99 | 1 |

FIG. 2C

METHODS FOR ASSESSING BINDING AFFINITY OF AN ANTIBODY VARIANT TO THE NEONATAL FC RECEPTOR

REFERENCE TO RELATED APPLICATIONS

This application claims the benefit of priority to U.S. Provisional Application Ser. No. 62/716,835, filed on Aug. 9, 2018. The entire contents of the foregoing application are incorporated herein by reference.

BACKGROUND

An immunoglobulin in general comprises two light chain polypeptides and two heavy chain polypeptides. Each of the heavy and light chain polypeptides contains a variable domain comprising binding regions that are able to interact with an antigen. Each of the heavy and light chain polypeptides comprises a constant region. The constant region of the heavy chain mediates the binding of the antibody i) to cells bearing an Fc gamma receptor (FcγR), such as phagocytic cells, or ii) to cells bearing the neonatal Fc receptor (FcRn). It also mediates the binding to some factors including factors of the classical complement system such as component (C1q).

The FcRn is also known as the MHC Class I-related receptor (see Ward, E. S. and Ober, R. J., Advances in Immunology 103 (2009) 77-115). In vivo, this receptor serves to regulate IgG levels and distribution throughout adult life (Ghetie, V., et al., Nat. Biotechnol. 15 (1997) 637-640; Israel, E. J., Immunology 89 (1996) 573-578; Junghans, R. P. and Anderson, C. L., Proc. Natl. Acad. Sci. USA 93 (1996) 5512-5516), and also has multiple other roles in diverse cell types and tissues (see, e.g., Akilesh, S., et al., Proc. Natl. Acad. Sci. USA 105 (2008) 967-972; Dickinson, B. L., et al., J. Clin. Invest. 104 (1999) 903-911; Kim, H., et al., Invest. Ophthalmol. Vis. Sci. 49 (2008) 2025-2029; Spiekermann, G. M., et al., J. Exp. Med. 196 (2002) 303-310; Zhu, X., et al., J. Immunol. 166 (2001) 3266-3276).

FcRn orthologs have been isolated from many species, including mouse, rat, man, sheep, cow, possum, pig, and camel (Adamski, F. M., et al., Mol. Immunol. 37 (2000) 435-444; Ahouse, J. J., et al., J. Immunol. 151 (1993) 6076-6088; Kacskovics, I., et al., J. Immunol. 164 (2000) 1889-1897; Kacskovics, I., et al., Dev. Comp. Immunol. 30 (2006) 1203-1215; Kandil, E., et al., J. Immunol. 154 (1995) 5907-5918; Mayer, B., et al., Immunology 107 (2002) 288-296; Schnulle, P. M. and Hurley, W. L., Vet. Immunol. Immunopathol. 91 (2003) 227-231; Simister, N. E. and Mostov, K. E., Nature 337 (1989) 184-187; Story, C. M., et al., J. Exp. Med. 180 (1994) 2377-2381), indicating that this receptor is present in essentially all mammalian species.

The multiple functions of FcRn are dependent on its ability to sort IgG away from lysosomal degradation within cells and release bound cargo during exocytic events at the plasma membrane (Ober, R. J., et al., Proc. Natl. Acad. Sci. USA 101 (2004) 11076-11081; Ober, R. J., et al., J. Immunol. 172 (2004) 2021-2029; Prabhat, P., et al., Proc. Natl. Acad. Sci. USA 104 (2007) 5889-5894). In addition, given the potential for modulating IgG trafficking pathways and behavior in vivo, engineering of antibodies to increase their half-life has expanded into an area of intense interest in the biopharmaceutical industry (Dall'Acqua, W. F., et al., J. Biol. Chem. 281 (2006) 23514-23524; Hinton, P. R., et al., J. Biol. Chem. 279 (2004) 6213-6216; Hinton, P. R., et al., J. Immunol. 176 (2006) 346-356; Shields, R. L., et al., J. Biol. Chem. 276 (2001) 6591-6604).

Given that FcRn is critical to protect IgG from lysosomal degradation and to regulate IgG half-life in circulation, it is important to determine factors that affect the binding between FcRn and IgG. The presence of post-translational modifications (PTMs), e.g., glycosylation, oxidation, and deamidation in the Fc region of an IgG may affect FcRn-IgG interaction and thereby influence the pharmacokinetic properties of an IgG in vivo. Thus, efficient and accurate methods for assessing the binding affinity of an antibody variant to FcRn and to characterize antibody variants are needed.

SUMMARY

FcRn plays an important role in the metabolic fate of antibodies. Thus, analysis and assessment of the interaction between FcRn and an antibody or antibody variant is extremely valuable to determine structural and functional integrity and predict the corresponding FcRn binding affinity of the antibody. The present invention provides methods to quickly and efficiently assess the effect of antibody variants, including sequence mutations, chemical and post-translational modifications (PTMs) on the binding between the antibody and FcRn. In particular, the present invention is based, at least in part, on the development of an online, two dimension liquid chromatography (2D-LC) method for assessing binding between antibody variants and FcRn. In one aspect, the online 2D-LC is coupled with mass spectrometry (MS). The present invention allows for differentiation of antibody variants by peak pattern, retention time profile by affinity chromatography and identification of these variants by mass spectrometry analysis.

In one aspect, the present invention provides a method for assessing binding affinity of an antibody variant to the neonatal Fc receptor (FcRn), or a fragment thereof, using an online two dimension liquid chromatography system, the method comprising contacting a first sample comprising antibody variants to an affinity chromatography stationary phase at an acidic pH, wherein the affinity chromatography stationary phase comprises immobilized FcRn or a fragment thereof, to thereby bind the antibody variants to the stationary phase; eluting the first sample from the stationary phase using a positive pH gradient, to obtain an eluted sample; contacting the eluted sample to a reverse phase chromatography stationary phase; and eluting the reverse phase chromatography in a mobile phase to obtain a second eluted sample, wherein antibody variants that elute ahead of a control sample are identified as having weaker binding affinity to FcRn than the control sample.

In one aspect, the method further comprises analyzing the second eluted sample using mass spectrometry (MS).

In one aspect, the acidic pH is a pH of about 6.0 or less. In another aspect, the positive pH gradient comprises an increase in pH from about pH 6.0 to about pH 8.8.

In one aspect, the sample is contacted to the affinity chromatography stationary phase in the presence of one or more buffer solutions. In another embodiment, the one or more buffer solutions comprise 80% of a first buffer solution at pH 5.5 and 20% of a second buffer solution at pH 8.8.

In another embodiment, the one or more buffer solutions comprise 80% of a first buffer solution comprising 20 mM MES/HCl, pH 5.5, 140 mM NaCl and 20% of a second buffer solution comprising 20 mM Tris/HCl, 140 mM NaCl, pH 8.8.

In one aspect, the pH gradient is generated using one or more buffer solutions. In another aspect, a first buffer solution comprises 20 mM MES/HCl, pH 5.5, 140 mM NaCl and a second buffer solution comprises 20 mM Tris/HCl, pH 8.8, 140 mM NaCl. In one aspect, the second buffer solution is increased from 20% to 100% to create the pH gradient.

In one aspect, the pH gradient is a linear gradient. In another aspect, the pH gradient is a step gradient. In a further aspect, the pH gradient mimics the physiological FcRn-IgG binding and dissociation process.

In one aspect, the flow rate of the affinity chromatography is about 0.08 mL/min. In another aspect, the flow rate of the reverse phase chromatography is about 0.3 mL/min.

In one aspect, the eluted sample is contacted to the reverse phase chromatography stationary phase in the presence of 0.1% formic acid in water (99%) and 0.1% formic acid in acetonitrile (1%).

In one aspect, the reverse phase chromatography uses a mobile phase comprising acetonitrile. In another aspect, the mobile phase comprises 0.1% formic acid in acetonitrile and 0.1% formic acid in water.

In one aspect, the eluting from the reverse phase chromatography results in desalting and/or the further separation of the antibody variants.

In one aspect, the antibody is of an IgG1, IgG2, or IgG4 isotype. In another aspect, the antibody is a bispecific antibody of an IgG4 isotype.

In a further aspect, the antibody variant contains a post-translational modification (PTM) of the antibody. In another aspect, the antibody variant is selected from the group consisting of an oxidized antibody, an antibody aggregate, a deamidated antibody, a glycoslyated antibody, and antibody variants with Fc mutations.

In another aspect, the present invention provides a method for assessing binding of an antibody variant to the neonatal Fc receptor (FcRn), or a fragment thereof, using an online two dimension liquid chromatography system, the method comprising contacting a first sample comprising antibody variants to an affinity chromatography stationary phase at an acidic pH, wherein the affinity chromatography stationary phase comprises immobilized FcRn or a fragment thereof, to thereby bind the antibody variants to the stationary phase; eluting the first sample from the affinity column using a positive pH gradient, to obtain an eluted sample; contacting the eluted sample to a reverse phase chromatography stationary phase; eluting the reverse phase chromatography in a mobile phase to obtain a second eluted sample; and analyzing the second eluted sample using mass spectrometry (MS), wherein antibody variants that elute ahead of a control sample are identified as having weaker binding to FcRn.

In one aspect of any of the foregoing aspects, the control sample comprises a wild-type antibody or an antibody that does not contain the same variant as the variant antibody being tested.

The present invention is illustrated by the following drawings and detailed description, which do not limit the scope of the invention described in the claims.

BRIEF DESCRIPTION OF THE DRAWINGS

FIG. 2A, FIG. 2B, and FIG. 2C depict an exemplary online 2D-LC-QE-HF-MS platform set-up and conditions for use. FIG. 2A depicts a 1290 Infinity II™ UHPLC (Agilent Technologies) and a Q Exactive HF Hybrid (QE-HF) Quadrupole-Orbitrap™ Mass Spectrometer (Thermo Fisher Scientific). FIG. 2B depicts exemplary flow rates and buffer solutions used for column 1 (an affinity chromatography column). FIG. 2C depicts exemplary flow rates and buffer solutions used for column 2 (a reverse phase chromatography column).

DETAILED DESCRIPTION

Figure 1:
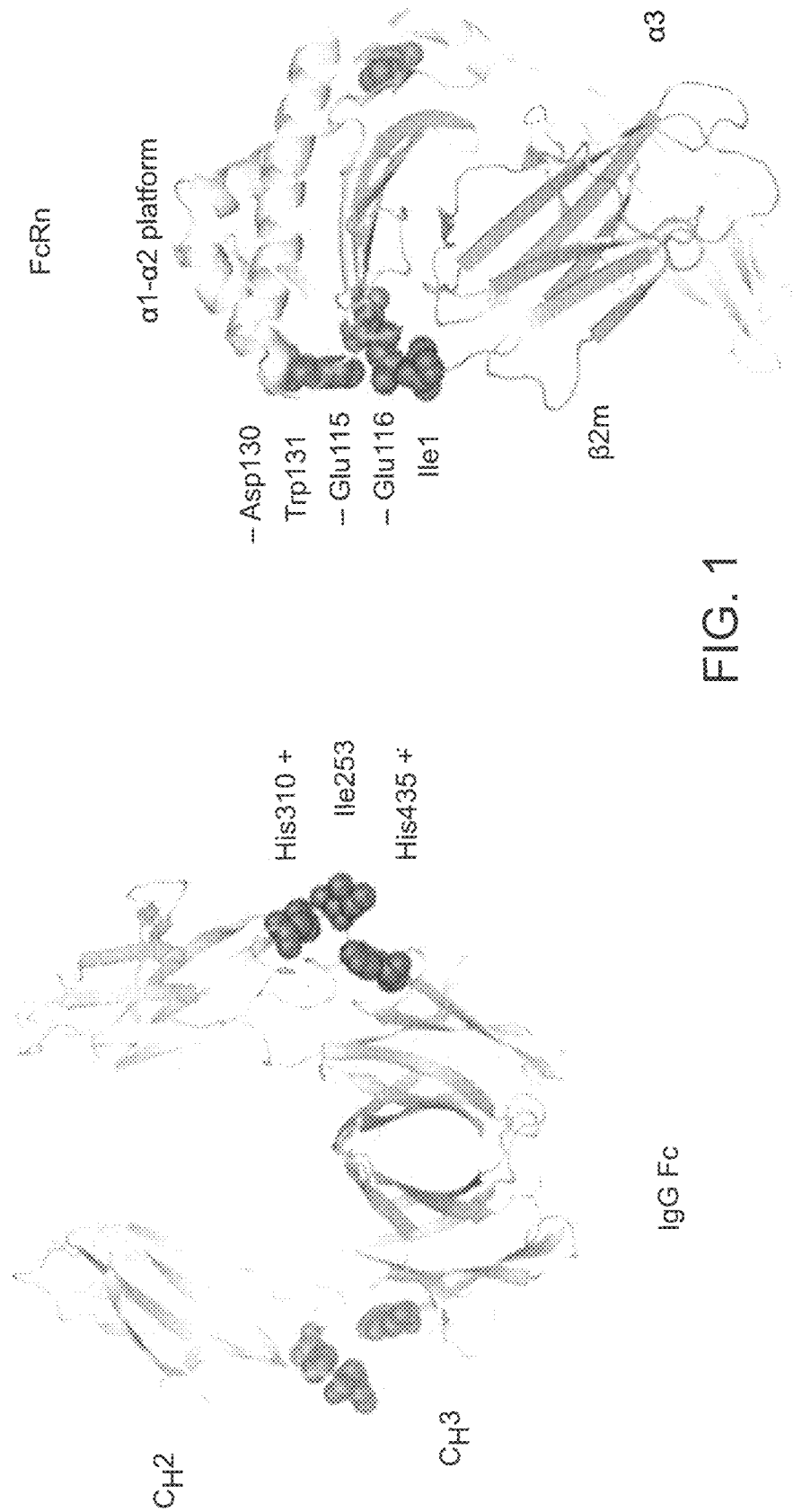
FIG. 1 depicts the primary binding site of FcRn on an IgG molecule.

The neonatal Fc receptor (FcRn) is a heterodimer consisting of an α-chain and a β2-microglobulin. FcRn binds IgG and albumin at an acidic pH (<6.5), but does not bind them, or releases the bound IgG/albumin, at physiological pH. In vivo, FcRn is critical to protect IgG from lysosomal degradation and to regulate the IgG half-life in circulation. FcRn binds IgG (including the IgG1, IgG2, IgG3 and IgG4 isotypes) with 1:1 or 2:1 stoichiometry under non-equilibrium or equilibrium conditions, respectively. The primary binding site of FcRn on an IgG molecule is located at the heavy chain constant region 2-heavy chain constant region 3 (CH2-CH3) interface within the Fc domain (see FIG. 1). The presence of antibody variants, including post-translational modifications (PTMs), in the Fc region of an IgG can affect FcRn-IgG interaction and thereby influence the pharmacokinetic properties of an IgG in vivo.

The present invention provides methods to quickly and efficiently assess the effect of antibody variants, including PTMs, e.g., glycosylation, oxidation, and deamidation variants, on the binding between the antibody and FcRn. In particular, the present invention is based, at least in part, on the development of an online, two dimension liquid chromatography (2D-LC) method for assessing binding between antibody variants and FcRn. In one aspect, the online 2D-LC is coupled with mass spectrometry (MS). The present invention allows for differentiation of antibody variants by peak pattern, retention time profile by affinity chromatography and identification of these variants by mass spectrometry analysis.

The present disclosure demonstrates the particular utility of affinity chromatography, followed by a second separation, e.g., via a reverse phase chromatography, in order to simultaneously isolate and/or analyze antibody variants and assess their binding affinity to FcRn.

The techniques of the present invention do not employ fixed standard parameters. Rather, the methods can be varied, for example, depending on the antibody variants being separated. For example, upon separation of a particular antibody variant in the first dimension using affinity chromatography, second dimensional parameters (e.g., column type, elution rate, elutant) can then be tuned to each individual fraction in order to optimize separation of individual antibody variants from that fraction. Additional separations using additional dimensions may be employed. Thus, each dimension may employ different parameters, and within each second, third, fourth, fifth, etc. dimension, separation parameters can vary from fraction to fraction.

In one aspect of the invention, the first dimension chromatography is conducted on an affinity medium, e.g., column, containing immobilized FcRn, or a fragment thereof. In one aspect, the affinity chromatography is conducted at an acidic pH. Antibodies and antibody variants bound to the FcRn affinity medium, e.g., column, are eluted using a pH gradient resulting in a first eluted sample. In one aspect, the pH gradient mimics the physiological FcRn-IgG binding and dissociation process. In another aspect, the pH gradient comprises an increase from about pH 6.0 to about pH 8.8. Subsequently, second dimension chromatography is conducted using the first eluted sample on a reverse phase medium, e.g., column, which is coupled to the affinity medium, e.g., column, resulting in the further separation of the antibody variants. Thus, in one aspect, the eluted antibody variants from the first dimension affinity chromatography are sequentially online fractionated, desalted and further separated using the second dimension reverse phase chromatography. In another aspect, the eluted antibody variants can be analyzed directly by mass spectrometry (MS) after two or more dimensional separations.

In one aspect, antibody variants that elute ahead of a control sample are identified as having weaker binding affinity to FcRn than the control, or parent, antibody, which lacks the same variation or modification. For example, the methods of the invention can distinguish: 1) IgGs with different Fcs and Fabs; 2) oxidized from non-oxidized antibodies; 3) aggregates from IgG monomers; 4) deaminated antibodies at FcRn binding region from non-deaminated antibodies or antibodies that are deaminated outside of the FcRn binding region; 5) glycosylated antibodies from non-glycosylated antibodies; and 6) antibodies with mutations in the Fc region from wild-type IgGs or IgGs having mutations outside of the Fc region.

The online, 2D-LC approach of the invention allows for minimized sample handling. In addition, sample contamination and sample loss are also reduced. In one aspect, the methods of the invention provide high-throughput analysis of antibody variants and assessment of antibody-FnRc binding.

As described in the Examples below, the methods described herein have been successfully applied to characterize monoclonal antibodies and their oxidation variants. Compared to the native antibodies, decreased binding was observed for antibodies exhibiting high levels of oxidation. This result has been confirmed by Biacore™ assay. Thus, the FcRn 2D-LC-MS methods of the invention can simultaneously evaluate FcRn-IgG binding, while identifying critical variants, e.g., PTMs, on the separated antibodies that can influence FcRn binding.

I. Definitions

In order that the present invention may be more readily understood, certain terms are first defined. In addition, it should be noted that whenever a value or range of values of a parameter are recited, it is intended that values and ranges intermediate to the recited values are also part of this invention.

In the following description, for purposes of explanation, specific numbers, materials and configurations are set forth in order to provide a thorough understanding of the invention. It will be apparent, however, to one having ordinary skill in the art that the invention may be practiced without these specific details. In some instances, well-known features may be omitted or simplified so as not to obscure the present invention.

The articles "a" and "an" are used herein to refer to one or to more than one (i.e., to at least one) of the grammatical object of the article. By way of example, "an element" means one element or more than one element.

The term "antibody" includes an immunoglobulin molecule comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region (CH). The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. As used herein, the term "antibody" is used in the broadest sense and encompasses various antibody structures, including but not limited to monoclonal antibodies, polyclonal antibodies, multispecific antibodies (e.g., bispecific antibodies), and antibody fragments which exhibit the ability to bind FcRn.

The term "Fc domain" "Fc region" or "immunoglobulin Fc" or "Ig Fc" is meant to refer to the immunoglobulin heavy chain "fragment crystallizable" region. The Fc domain is composed of two identical protein fragments, derived from the second and third constant domains (CH2 and CH3) of the antibody's two heavy chains; IgM and IgE Fc regions contain three heavy chain constant domains (CH domains 2-4) in each polypeptide chain. Generally, an Fc domain is capable of interacting with a second Fc domain to form a dimeric complex. The Fc domain may be capable of binding cell surface receptors called Fc receptors and/or proteins of the complement system or may be modified to reduce or augment these binding activities. The Fc domain may be derived from IgG, IgA, IgD, IgM or IgE antibody isotypes (referred to herein as an IgG Fc domain, an IgA Fc domain, an IgD Fc domain, an IgM Fc domain, and an IgE Fc domain, respectively). The Fc domain may effect immune activity including opsonization, cell lysis, degranulation of mast cells, basophils, and eosinophils, and other Fc receptor-dependent processes; activation of the complement pathway; and protein stability in vivo. In one aspect, the Fc domain is of human origin.

The term "neonatal Fc receptor" or "FcRn" denotes the human neonatal Fc receptor. FcRn functions to salvage IgG from the lysosomal degradation pathway, resulting in reduced clearance and long half-life. The FcRn is a heterodimeric protein consisting of two polypeptides: a 50 kDa class I major histocompatibility complex-like protein ($\alpha$-FcRn) and a 15 kDa $\beta$-2-microglobulin (($\beta$2m). FcRn binds with high affinity to the CH2-CH3 portion of the Fc domain of IgG. The interaction between IgG and FcRn is pH dependent and occurs in a 1:2 stoichiometry, with one IgG binding to two FcRn molecules via its two heavy chains (Huber, A. H., et al., J. Mol. Biol. 230 (1993) 1077-1083). FcRn binding occurs in the endosome at acidic pH (pH<6.5) and IgG is released at the neutral cell surface (pH of about 7.4). The pH-sensitive nature of the interaction facilitates the FcRn-mediated protection of IgGs pinocytosed into cells from intracellular degradation by binding to the receptor within the acidic environment of endosomes. FcRn then facilitates the recycling of IgG to the cell surface and subsequent release into the blood stream upon exposure of the FcRn-IgG complex to the neutral pH environment outside the cell. In one aspect of the invention, the FcRn can be selected from human FcRn, cynomolgus FcRn, mouse FcRn, rat FcRn, sheep FcRn, dog FcRn and rabbit FcRn.

The term "FcRn binding portion of an Fc region" denotes the part of an antibody heavy chain polypeptide that extends approximately from Eu position 243 to Eu position 261 and approximately from Eu position 275 to Eu position 293 and approximately from Eu position 302 to Eu position 319 and approximately from Eu position 336 to Eu position 348 and approximately from Eu position 367 to Eu position 393 and Eu position 408 and approximately from Eu position 424 to Eu position 440.

As used herein, the terms "antibody variant" refers to any variants of a protein, e.g., an antibody or antigen-binding portion thereof, which are in the Fc region of an IgG and/or affect FcRn-IgG interaction or binding. Antibody variants include post-translational modifications (PTMs) of an antibody. By "post-translational modification" is meant a change to an antibody that occurs after that antibody is translated from mRNA. Post-translational modifications include but are not limited to the addition or deletion of biochemical functional groups such as acetate, phosphate, various lipids and carbohydrates. Non-limiting examples of antibody variants include, but are not limited to, antibody fragments, aggregates, acetylation variants, deamidation variants, oxidation variants, glycation variants, ubiquitination variants, glycosylation variants, charge variants, oligomerization variants, and antibodies with mutations in the Fc region of the antibody.

Antibody variants also include antibodies having an amino acid sequence that differs from the amino acid sequence of a parent molecule. In one aspect, such molecules have one or more alterations, insertions, or deletions. In one aspect the modified antibody comprises an amino acid sequence comprising at least a portion of an Fc-region which is not naturally occurring. Such molecules have less than 100% sequence identity with the parent antibody or parent fusion polypeptide. In one aspect the variant antibody has an amino acid sequence that has from about 75% to less than 100% amino acid sequence identity with the amino acid sequence of the parent antibody, from about 80% to less than 100%, from about 85% to less than 100%, from about 90% to less than 100%, or from about 95% to less than 100% amino acid sequence identity with the amino acid sequence of the parent antibody. In one aspect, the parent antibody and the variant antibody differ by one (a single), two or three amino acid residue(s).

The term "control sample" refers to a sample comprising a parent antibody or a reference antibody which lacks the same variation or modification as the corresponding antibody variant being tested. In one aspect, a control antibody is a wild-type antibody. In another aspect, a control antibody is an antibody lacking the same variation in the Fc region as the corresponding antibody variant being tested.

The term "positive linear pH gradient" denotes a pH gradient starting at a low (i.e., more acidic) pH value and ending at a higher (i.e., less acidic, neutral or alkaline) pH value. In one aspect, the positive linear pH gradient starts at a pH value of about pH 5.5, pH 5.6, pH 5.7, pH 5.8, pH 5.9, pH 6.0, pH 6.1, pH 6.2, pH 6.3, pH 6.4, or pH 6.5 and ends at a pH value of about pH 8.0, pH 8.5, pH 8.6, pH 8.7, pH 8.8, or pH 9.

"Chromatography" is a chemical separation technique that involves passing a mixture dissolved in a "mobile phase" through a stationary phase, which separates the analyte to be measured from other molecules in the mixture based on differential partitioning between the mobile and stationary phases.

"Liquid chromatography" or "LC" as used herein is a separation technique in which the mobile phase is a liquid. Liquid chromatography can be carried out either in a column or a plane. In one aspect, the LC methods and equipment of the invention are coupled with a mass spectrometer.

The term "mass spectrometer" refers to a device capable of detecting specific molecular species and measuring their accurate masses. The term is meant to include any molecular detector into which a polypeptide or peptide may be eluted for detection and/or characterization. In the preferred MS procedure, a sample, e.g., an elution sample, is loaded onto the MS instrument, and undergoes vaporization. The components of the sample are ionized by one of a variety of methods (e.g., by impacting them with an electron beam), which results in the formation of positively charged particles (ions). The positive ions are then accelerated by a magnetic field.

Liquid chromatography-mass spectrometry ("LC-MS") is a technique that combines the physical separation capabilities of liquid chromatography, or high performance LC (HPLC), with the mass analysis capabilities of mass spectrometry.

The term "buffer solution" or "buffer" denotes a substance that when in solution can level changes of the pH value of the solution e.g., due to the addition or release of acidic or basic substances. The term "elution buffer" refers to a buffer solution that when brought into contact with the immobilized binding partner (i.e., FcRn) and substrate, results in the dissociation of the antibody or antibody variant and from the immobilized binding partner into the elution buffer. Determining the salt, pH and ionic conditions necessary for such functionality is well within the ordinary skill in the art. A portion of the elution buffer may be directly transferred to a mass spectrometer. Alternatively, a portion of the elution buffer is subject to further manipulation, e.g., to concentrate, to sort, or to order the antibodies contained therein.

In one aspect, a portion of the elution buffer is analyzed using an LC-MS device, as described herein. In one aspect, the LC device separates and orders the antibody variants (e.g., by retention time) present in the elution buffer prior to the MS measurement of their accurate mass. In one aspect, the retention times of the antibody variants present in the elution buffer are matched with the measured accurate mass of the antibody variants. In another aspect, the relative position of antibody variant elution is additionally aligned with a set of antibody variants the LC elution order and/or time of which is known (i.e., reference antibody variants or control antibodies or parent antibodies). Mechanisms for directing buffers from liquid chromatography to mass spectrometers may be found, for example, in U.S. Pub. No. 20080217254, the contents of which are incorporated by reference herein.

A "solid phase" denotes a non-fluid substance, and includes particles (including microparticles and beads) made from materials such as polymer, metal (paramagnetic, ferromagnetic particles), glass, and ceramic; gel substances such as silica, alumina, and polymer gels; capillaries, which may be made of polymer, metal, glass, and/or ceramic;

zeolites and other porous substances; electrodes; microtiter plates; solid strips; and cuvettes, tubes or other spectrometer sample containers. A solid phase component of an assay is distinguished from inert solid surfaces in that a "solid support" contains at least one moiety on its surface, which is intended to interact chemically with a molecule. A solid phase may be a stationary component, such as a chip, tube, strip, cuvette, or microtiter plate, or may be non-stationary components, such as beads and microparticles. Microparticles can also be used as a solid support for homogeneous assay formats. A variety of microparticles that allow both non-covalent or covalent attachment of proteins and other substances may be used. Such particles include polymer particles such as polystyrene and poly(methylmethacrylate); gold particles such as gold nanoparticles and gold colloids; and ceramic particles such as silica, glass, and metal oxide particles. See for example Martin, C. R., et al., Analytical Chemistry—News & Features, May 1 (1998) 322A-327A, which is incorporated herein by reference.

The term "isolated" refers to a composition, compound, substance, or molecule altered by the hand of man from the natural state. For example, a composition or substance that occurs in nature is isolated if it has been changed or removed from its original environment, or both. For example, a polynucleotide or a polypeptide naturally present in a living animal is not isolated, but the same polynucleotide or polypeptide separated from the coexisting materials of its natural state is isolated, as the term is employed herein.

II. Affinity Chromatography

Figure 2A:
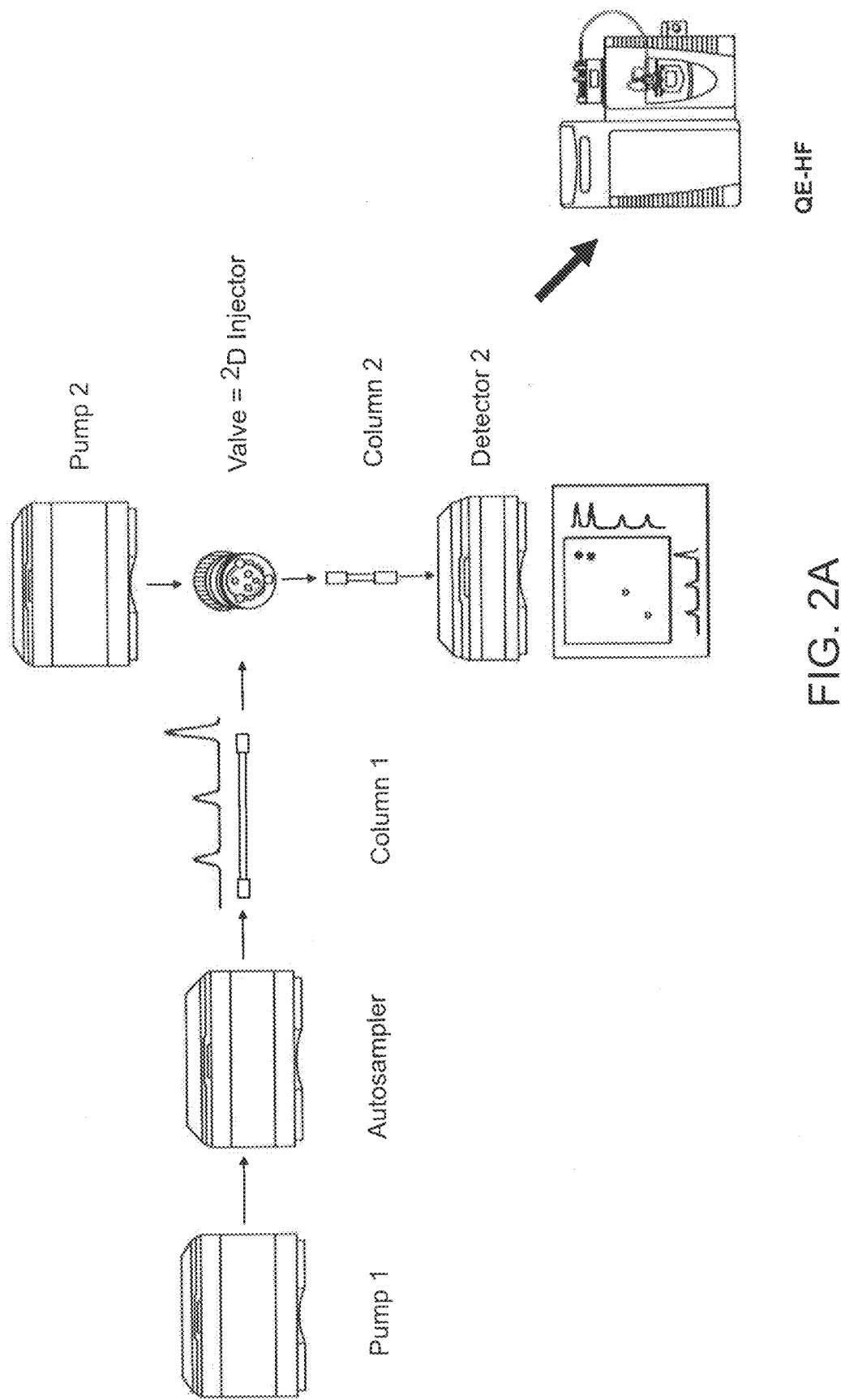

The present invention includes methods for characterizing antibody variants and assessing antibody binding to FcRn using an affinity chromatography medium. In one aspect of the invention, the affinity chromatography medium used in the methods of the invention is coupled online with one or more additional chromatography media, such as a reverse phase chromatography medium. In another aspect, the one or more chromatography media of the invention are coupled directly to mass spectrometry (MS). For example, FIGS. 2A, 2B, and 2C depict an exemplary online 2D-LC-QE-HF-MS platform set-up and conditions for use. FIG. 2B depicts exemplary flow rates and buffers used for column 1 (an affinity chromatography column) and FIG. 2C depicts exemplary flow rates and buffers used for column 2 (a reverse phase chromatography column). The online, 2D-LC approach of the invention allows for minimized sample handing and a reduction in sample contamination and sample loss.

Affinity chromatographic media is capable of selectively or specifically binding to the protein of interest ("capture"). An example of such chromatographic material includes chromatographic material comprising an Fc binding protein, such as FcRn, or a fragment thereof. A fragment of an FcRn is a fragment that is capable of binding to the Fc portion of an IgG. In specific aspects, the affinity chromatography step of the present invention involves subjecting a sample comprising antibody variants to a column comprising immobilized FcRn, or a fragment thereof. In certain aspects, FcRn, or a fragment thereof, is useful for affinity purification and isolation of a variety of antibody isotypes, particularly human IgG1, IgG2, IgG3 and IgG4 isotypes.

In one aspect, the FcRn affinity chromatographic medium of the invention allows the assessment of mAb samples with respect to their pH-dependent FcRn interaction. In one aspect, the affinity chromatography medium allows assessment of antibody variant affinity to FcRn in a pH gradient from about pH 5.5 to about pH 8.8. In one aspect, the chromatography medium allows assessment of antibody variant affinity to FcRn in a pH gradient from about pH 6.0 to about pH 8.8.

In one aspect, an affinity chromatography medium used in the methods of the invention is an FcRn affinity chromatography column packed with resin comprising immobilized wild-type FcRn, or fragments thereof. In another aspect, the affinity chromatography medium used in the methods of the invention comprises an immobilized non-covalent complex of FcRn, or fragments thereof, and beta-2-microglobulin, as affinity chromatography ligand.

In one aspect, an FcRn affinity chromatography medium used in the methods of the invention is an FcRn affinity chromatography column available from Roche CustomBiotech (Mannheim, Germany; cat. No. 08128057001) (see, e.g., Schlothauer et al., Mabs. 2013; 5(4):576-586; Sand et al. Front Immnol. 2014; 5:682; and Strache et al., Mabs. 2014; 6(5):1229-1242, the contents of which are hereby incorporated herein by reference). In one aspect, the affinity chromatography medium used in the methods of the invention is described in, for example, PCT Publication No. WO2013120929 and U.S. Patent Publication No. US2015/0018241, the contents of which are hereby incorporated herein by reference.

Affinity chromatography (also called affinity purification) makes use of specific binding interactions between molecules. A particular ligand is chemically immobilized or "coupled" to a solid support so that when a complex mixture is passed over the column, those molecules having specific binding affinity to the ligand become bound. After other sample components are washed away, the bound molecule is stripped from the support, resulting in its purification from the original sample.

Most commonly, ligands are immobilized or "coupled" directly to solid support material by formation of covalent chemical bonds between particular functional groups on the ligand and reactive groups on the support. Ligands that bind to general classes of proteins (e.g., antibodies) are commercially available in pre-immobilized forms ready to use for affinity purification. Alternatively, more specialized ligands such as specific antibodies or antigens of interest can be immobilized using one of several commercially available activated affinity supports; for example, a peptide antigen can be immobilized to a support and used to purify antibodies that recognize the peptide.

Most affinity purification procedures involving protein: ligand interactions use binding buffers at physiologic pH and ionic strength, such as phosphate buffered saline (PBS). This is especially true when antibody:antigen or native protein: protein interactions are the basis for the affinity purification. Once the binding interaction occurs, the support is washed with additional buffer to remove non-bound components of the sample. Nonspecific (e.g., simple ionic) binding interactions can be minimized by adding low levels of detergent or by moderate adjustments to salt concentration in the binding and/or wash buffer. Finally, elution buffer is added to break the binding interaction and release the target molecule, which is then collected in its purified form.

Elution buffers dissociate binding partners by extremes of pH (low or high), high salt (ionic strength), the use of detergents or chaotropic agents that denature one or both of the molecules, removal of a binding factor or competition with a counter ligand.

In one aspect, the sample comprising antibody variants is contacted to the FcRn affinity column at a first pH value and the antibody is recovered from the FcRn affinity column at a second pH value.

In one aspect of all previous aspects the pH is a gradient from about pH 5.5 to about pH 8.8. In one aspect the pH is a gradient from about pH 5 to pH 6, or from about pH 6 to about pH 7, or from about pH 7 to about pH 8.

In one aspect the first pH value is about pH 3.5 to about pH 7.5. In one aspect the first pH value is about pH 4 to about pH 7. In one aspect the first pH value is about pH 4.5 to about pH 6.5. In one aspect the first pH value is about pH 5 to about pH 6. In one aspect the first pH value is about pH 5 or about pH 5.5 or about pH 6.

In one aspect the first pH value is selected from about pH 3.5, about pH 3.6, about pH 3.7, about pH 3.8, about pH 3.9, about pH 4.0, about pH 4.1, about pH 4.2, about pH 4.3, about pH 4.4, about pH 4.5, about pH 4.6, about pH 4.7, about pH 4.8, about pH 4.9, about pH 5.0, about pH 5.1, about pH 5.2, about pH 5.3, about pH 5.4, about pH 5.5, about pH 5.6, about pH 5.7, about pH 5.8, about pH 5.9, about pH 6.0, about pH 6.1, about pH 6.2, about pH 6.3, about pH 6.4, about pH 6.5, about pH 6.6, about pH 6.7, about pH 6.8, about pH 6.9, about pH 7.0, about pH 7.1, about pH 7.2, about pH 7.3, about pH 7.4, and about pH 7.5.

In one aspect the second pH value is about pH 8 to about pH 9.5. In one aspect the second pH value is about pH 8.5 to about pH 9. In one aspect the second pH value is about pH 8.8.

In one aspect the second pH value is selected from about pH 8.0, about pH 8.1, about pH 8.2, about pH 8.3, about pH 8.4, about pH 8.5, about pH 8.6, about pH 8.7, about pH 8.8, about pH 8.9, about pH 9.0, about pH 9.1, about pH 9.2, about pH 9.3, about pH 9.4, and about pH 9.5.

In one aspect each of the given first pH values of about pH 3.5, about pH 3.6, about pH 3.7, about pH 3.8, about pH 3.9, about pH 4.0, about pH 4.1, about pH 4.2, about pH 4.3, about pH 4.4, about pH 4.5, about pH 4.6, about pH 4.7, about pH 4.8, about pH 4.9, about pH 5.0, about pH 5.1, about pH 5.2, about pH 5.3, about pH 5.4, about pH 5.5, about pH 5.6, about pH 5.7, about pH 5.8, about pH 5.9, about pH 6.0, about pH 6.1, about pH 6.2, about pH 6.3, about pH 6.4, about pH 6.5, about pH 6.6, about pH 6.7, about pH 6.8, about pH 6.9, about pH 7.0, about pH 7.1, about pH 7.2, about pH 7.3, about pH 7.4, and about pH 7.5 is combined with each of the given second pH values of about pH 8.0, about pH 8.1, about pH 8.2, about pH 8.3, about pH 8.4, about pH 8.5, about pH 8.6, about pH 8.7, about pH 8.8, about pH 8.9, about pH 9.0, about pH 9.1, about pH 9.2, about pH 9.3, about pH 9.4, and about pH 9.5.

The recovering of antibody bound to the FcRn affinity medium as described herein is by a linear gradient elution. In one aspect, the linear gradient is a pH gradient or a conductivity gradient. In another aspect, the linear gradient is a positive pH gradient.

In principle, any buffer substance can be used in the methods as reported herein. In one aspect, a pharmaceutically acceptable buffer substance is used with the affinity chromatography medium, such as e.g., phosphoric acid or salts thereof, acetic acid or salts thereof, citric acid or salts thereof, morpholine, 2-(N-morpholino) ethanesulfonic acid (MES) or salts thereof, histidine or salts thereof, glycine or salts thereof, tris(hydroxymethyl)aminomethane (TRIS) or salts thereof, (4-(2-hydroxyethyl)-1-piperazineethanesulfonic acid (HEPES) or salts thereof.

In one aspect, the buffer substance is selected from phosphoric acid or salts thereof, or acetic acid or salts thereof, or citric acid or salts thereof, or histidine or salts thereof.

In one aspect, the buffer substance has a concentration of from 10 mM to 500 mM. In one aspect, the buffer substance has a concentration of from 10 mM to 300 mM. In one aspect, the buffer substance has a concentration of from 10 mM to 250 mM. In one aspect, the buffer substance has a concentration of from 10 mM to 100 mM. In one aspect, the buffer substance has a concentration of from 15 mM to 50 mM. In one aspect, the buffer substance has a concentration of about 20 mM.

In one aspect, two buffer substances are used. In one aspect, the buffer substance in the first solution and the buffer substance in the second solution are the same buffer substance. In one aspect the buffer substance in the first solution and the buffer substance in the second solution are different buffer substances.

In one aspect the first buffer solution (buffer A) has a pH value of about pH 3.5 to about pH 7.5. In one aspect the first buffer solution has a pH value of about pH 5 to about pH 6. In one aspect the first buffer solution has a pH value of about pH 5.5.

In one aspect the second buffer solution (buffer B) has a pH value of about pH 7.0 to about pH 9.5. In one aspect the second buffer solution has a pH value of about pH 8 to about pH 9. In one aspect the second buffer solution has a pH value of about pH 8.2 to about pH 8.8.

An exemplary first buffer solution comprises 20 mM MES/HCl and 140 mM NaCl, adjusted to pH 5.5 (see FIG. 2B, column 1, buffer A). An exemplary second buffer solution comprises 20 mM TRIS/HCl and 140 mM NaCl, adjusted to pH 8.8 (see FIG. 2B, column 1, buffer B). An additional exemplary second buffer solution comprises 20 mM HEPES adjusted to pH 8.6. Another exemplary second buffer solution comprises 20 mM TRIS adjusted to pH 8.2.

In one exemplary aspect, the initial buffering solution comprises about 80% buffer A (e.g., 20 mM MES and 140 mM NaCl, adjusted to pH 5.5) and about 20% buffer B (e.g., 20 mM TRIS and 140 mM NaCl, adjusted to pH 8.8). Subsequently, buffer A is decreased to about 0%, 1%, 2%, 3%, 4%, or 5% and buffer B is increased to about 95%, 96%, 97%, 98%, 99%, or 100% over time in a positive pH gradient to elute the sample from the affinity chromatography medium. In one aspect, buffer A is subsequently increased to about 80% and buffer B is subsequently decreased to about 20%.

In one aspect, the time (minutes) for the pH gradient is set forth in FIG. 2B. Other appropriate times for the pH gradient will be understood by one of ordinary skill in the art.

In one aspect the buffer solution comprises an additional salt. In one aspect the additional salt is selected from sodium chloride, sodium sulphate, potassium chloride, potassium sulfate, sodium citrate, or potassium citrate. In one aspect comprises the buffered solution of from 50 mM to 1000 mM of the additional salt. In one aspect comprises the buffer solution of from 50 mM to 750 mM of the additional salt. In one aspect comprises the buffer solution of from 50 mM to 500 mM of the additional salt. In one aspect comprises the buffer solution of from 50 mM to 750 mM of the additional salt. In one aspect comprises the buffer solution about 50 mM to about 300 mM of the additional salt.

In one aspect the first and/or second solution comprises sodium chloride. In one aspect the first and/or second solution comprises of about 50 mM to about 300 mM sodium chloride.

III. Reverse Phase Chromatography

Reverse phase liquid chromatography (RPC or RPLC), also referred to as hydrophobic chromatography, includes any chromatographic method that uses a hydrophobic stationary phase. Reverse phase chromatography is a technique using alkyl chains covalently bonded to the stationary phase particles in order to create a hydrophobic stationary phase, which has a stronger affinity for hydrophobic or less polar compounds. In RPC, a molecule in solution binds to the hydrophobic surface or hydrophobic ligand of a chromatographic resin. The partitioning of the molecule between the solution and the resin occurs as a result of hydrophobic interactions between the molecule with hydrophobic patches at its surface and the hydrophobic surface on the resin. A solvent of increasing hydrophobicity is subsequently used to dissociate or elute the bound molecule at a point at which the hydrophobic interaction between the exposed patches and the resin is less favorable than the interaction between the bound molecule and the solvent. The molecule then releases from the resin and elutes. Separation of different molecules in the same solution occurs if the molecules have different hydrophobicity and therefore elute at different point in time when the hydrophobicity of the eluting solvent is increased.

In general, RPC is capable of distinguishing between molecules with very small differences in hydrophobicity and it is thus regarded as a powerful separation tool and a preferred method in analytical chromatography.

RPC column medium is made of a resin to which as hydrophobic material may be attached. Stationary phases for reverse phase chromatography include, but are not limited to, silylated silica (i.e., wherein silica has been treated with $RMe_{2SiCl}$, and wherein R is a straight chain alkyl group such as $C_{18}H_{37}$, $C_8H_{17}$, or $C_{47}$), diphenyl resins, divinylbenzene resins, and carbon resins. Another typical resin material is polystyrene; hydrophobic ligands may optionally be attached. In case of substituted resins, the resin is substituted with a hydrophobic ligand, typically selected from (but not limited to) aliphates, such as $C_2$, $C_4$, $C_6$, $C_8$, $C_{10}$, $C_{12}$, $C_{14}$, $C_{16}$, or $C_{18}$ or derivates of these, e.g., cyanopropyl (CN-propyl), or branched aliphates, or benzene-based aromates, such as phenyl, or other polar or non-polar ligands. The ligand may be a mixture of two or more of these ligands. Suitable polystyrene based resins include, without limitation, resins supplied by Rohm Haas (e.g., Amberlite XAD or Amberchrom CG), Polymer Labs (e.g., PLRP-S), GE Healthcare (e.g., Source RPC), Applied Biosystems (e.g., Poros R).

In certain aspects, reverse phase chromatography includes the use of a graphitized-carbon resin (e.g., porous graphitized carbon, PGC).

The manufacturing processes for and optimal features of the RPC material often require that a linking group, also called a spacer, is inserted between the resin and the ligand.

Features for RPC media which improve performance with large proteins such as antibodies include, for example, wide-pore phases, such as organic monoliths with macropore sizes of between about 1-5 μm, core-shell particles of about 2.5-5 μm, and fully porous sub-2 μm UHPLC columns.

Typical mobile phases for reverse phase chromatography include relatively polar elution buffer solutions, such as water and polar organic solvents (e.g., acetonitrile, organic alcohols). Retention time is increased by the addition of polar solvent to the mobile phase and decreased by the addition of more hydrophobic solvent. The retention time is therefore longer for analytes which are more non-polar in nature, allowing polar analytes to elute more readily.

In one aspect, a buffer is a mixture of an acid (HA) and its conjugated base ($A^-$). A buffer is capable of resisting changes in pH as the result of addition of acid or base. This resistance (buffer capacity) is largest when pH is close to the pKa of the acid HA. A mixture of an acid and the conjugated base is regarded as a buffer if the pH of the solution is within two pH units, such as within one pH unit from the pKa value of the acid. Examples of buffers which can be applied in the present invention include acetate buffers, phosphate buffers, citric acid buffers, lactic acid buffers, TRIS buffers, CHAPS buffers, borate buffers, HEPES buffers, carbonate buffers, histidine buffers, MES buffers, ascorbic buffers, and mixtures of two or more of these. It is standard in the art to add trifluoro acetic acid (TFA) to RPC solvents to adjust pH.

Typical buffer concentrations to be used in the present invention are between 0.02 and 20 (w/w) %, such as between 0.05 and 5 (w/w) %, such as between 0.1 and 0.2 (w/w) %.

Typically pH of solvents is within the range of 1-13, such as 2-13, such as 3-13, such as 3.5-13, such as 4-13, such as 4.5-13, such as 5-13, such as 5.5-13, such as 6-13, such as 6.5-13, such as 7-13, such as 7.5-13, such as 8-13, such as 1-12, such as 1-11, such as 1-10, such as 1-9.5, such as 1-9, such as 1-8.5, such as 2-10, such as 3-9.5, such as 3.5-9.5, such as 4-9.5, such as 4.5-9.5, such as 5-9.5, such as 5.5-9.5, such as 6-9.5, such as 6.5-9.5, such as 7-9.5, such as 7.5-9.5, such as 8-9.5, such as 3-9, such as 3.5-9, such as 4-9, such as 4.5-9, such as 5-9, such as 5.5-9, such as 6-9, such as 6.5-9, such as 7-9, such as 7.5-9, such as 8-9, such as 3-8.5, such as 3.5-8.5, such as 4-8.5, such as 4.5-8.5, such as 5-8.5, such as 5.5-8.5, such as 6-8.5, such as 6.5-8.5, such as 7-8.5, such as 7.5-8.5, such as 8-8.5, such as 3-8, such as 3.5-8, such as 4-8, such as 4.5-8, such as 5-8, such as 5.5-8, such as 6-8, such as 6.5-8, such as 7-8, such as 7.5-8.

In one aspect, the solvent used to elute the protein comprises a salt in solution. The term salt is used for ionic compounds composed of positively charged cations (X) and negatively charged anions (Y), so that the product is neutral and without a net charge. Both X and Y may be multiply charged so that the ratio X:Y may be different from 1:1.

The salt used together with the buffer does not have any significant buffering capacity at the pH achieved with the specific buffer used and are thus not part of the buffer system itself. In one aspect, the pKa of the salt is at least one pH unit removed from the pKa of the buffer used. In a further aspect, the pKa of the salt is at least one pH unit removed from the pKa of the buffer used. The choice of salt to be used together with the buffering system will naturally depend on the choice of buffer, but when working at a pH range usual for handling proteins, examples of salts which can be applied in the present invention could include halides, such as chlorides, bromides, iodines; sulphates; borates; lactates; and citrates, and mixtures of two or more thereof. Examples of the positively charged counter ion include sodium; potassium; magnesium; calcium; and ammonium. Specific examples of salts include potassium chloride; sodium chloride; ammonia chloride and potassium lactate.

Typical salt concentrations to be used in the present invention are between 0.02 and 30 (w/w) %, such as between 0.05 and 10 (w/w) %, such as between 0.16 and 1.1 (w/w) %.

In one aspect, the elution buffer solution used in the methods of the present invention comprises an aqueous solvent comprising water and an organic component. Typical organic components include acetonitrile or alcohols.

In one aspect, the organic component is an alcohol, and in one aspect, the solvent is a mixture of water and an alcohol. Particular mentioning is made of mono-alcohols, i.e. alcohols comprising only one alcohol group. Examples of mono-alcohols which can be used in the methods of the present invention include methanol, ethanol, 1-propanol and 2-propanol, and mixtures of two or more thereof. In another aspect, the organic component is acetonitrile, and in one aspect, the solvent is a mixture of water and acetonitrile.

In one aspect, the proteins are eluted with an increasing hydrophobicity of the solvent, i.e., by increasing the concentration of the organic compound. The concentration of the solvent used to load the protein on to the column depends on the nature of the protein and the hydrophobicity of the organic compound. This solvent is often referred to as the equilibration solvent as the column has typically been washed or equilibrated with one or more column volumes of this solvent prior to the loading of the protein to the column. A typical concentration of the organic compound in the equilibrating solvents is from 1-90%, such as 1-45%, 10-70%, 10-60%, or 20-50%. The concentration is upward limited by the denaturing effect of the organic component. If the concentration is too high, there is a risk that the protein may irreversible denature. During elution of the protein, the concentration of the organic component in the solvent is raised, typically to concentrations from 5-96%, such as 10-95%, 20-90%, 30-90%, or 40-80%, 45%, or 90%.

Elution derived from the increase in the concentration of the organic component in the solvent (often referred to as the gradient) may be brought about in a number of ways. The gradient may be linear, stepped comprising one or more steps, isocratic or curved. Elution may also be performed in isocratic mode, that is, by constant organic component concentration. The elution scheme may also be applied in any combination of the above gradients and isocratic elution mode, e.g., an elution scheme may be a linear gradient followed by an isocratic elution followed by a step and followed by a linear gradient again, or it may be a linear gradient followed by another linear gradient. Aside from mobile phase polarity, other mobile phase modifiers can affect analyte retention. For example, the addition of inorganic salts causes a linear increase in the surface tension of aqueous solutions, and because the entropy of the analyte-solvent interface is controlled by surface tension, the addition of salts tend to increase the retention time. Another important component is pH since this can change the hydrophobicity of the analyte. For this reason most methods use a buffering agent, such as sodium phosphate to control the pH. An organic acid such as formic acid or trifluoroacetic acid is often added to the mobile phase. These serve multiple purposes by controlling the pH, neutralizing the charge on any residual exposed silica on the stationary phase and acting as ion pairing agents to neutralize charge on the analyte. The effect varies depending on use but generally improves the chromatography.

In one aspect of the invention, two buffer solutions are used for elution. In one aspect, the buffer substance in the first solution and the buffer substance in the second solution are the same buffer substance. In one aspect the buffer substance in the first solution and the buffer substance in the second solution are different buffer substances.

An exemplary first buffer solution comprises formic acid in water, e.g., 0.1% formic acid in water (see FIG. 2C, column 2, buffer A). An exemplary second buffer solution comprises formic acid in acetonitrile, e.g., 0.1% formic acid in acetonitrile (see FIG. 2C, column 2, buffer B).

In one exemplary aspect, the initial buffering solution comprises about 99% buffer A (e.g., 0.1% formic acid in water) and about 1% buffer B (e.g., 0.1% formic acid in acetonitrile). Subsequently, buffer A is decreased to about 55%, 50%, 45%, 30%, 25%, 20%, 15%, or 10% and buffer B is increased to about 45%, 50%, 55%, 60%, 65%, 70%, 75%, 80%, 85%, 90%, 95% or 100% over time in a pH gradient to elute the sample from the reverse chromatography medium. In one aspect, buffer A is subsequently increased to about 99% and buffer B is subsequently decreased to about 1%.

In one aspect, the time (minutes) for the reverse chromatography portion of the method is set forth in FIG. 2C. Other appropriate times will be understood by one of ordinary skill in the art.

Other parameters in the methods of the present invention include load, i.e., amount of protein which is loaded to the column and flow rate. These parameters may be optimized through experiments which are known to the person skilled in the art. The protein is typically loaded onto the column in a concentration of at least about 0.1 mg per mL of resin, such as, e.g., at least about 0.2 mg, 0.5 mg, 1 mg, 2 mg, 5 mg, 10, or 20 mg per mL of resin; or in the range of 0.1-200 mg, such as, e.g., 0.1-100 mg, 0.5-100 mg, 1-50 mg, or 2-30 mg per mL of resin; preferably the load is at least 1 mg per mL resin. Measurement of packed resin volume is typically done in suspension or similar mode.

The protein is typically applied at a flow of 1-200 column volumes per hour (CV/h), such as at least 1 CV/h, such as at least 2 CV/h, such as at least 3 CV/h, such as at least 4 CV/h, such as at least 5 CV/h, such as at least 6 CV/h, such as at least 8 CV/h, such as at least 10 CV/h, such as at least 12 CV/h, e.g. at least 20 CV/h or at least 40 CV/h or at least 80 CV/h, e.g., 80-120 CV/h.

In one aspect, the RPC column used in the methods of the invention is the MAbPac™ RP Column (Thermo Scientific™). This column is a reverse phase liquid chromatography column designed for monoclonal antibody characterization, including the separation of antibody variants. The stationary phase is compatible with mass spectrometry-friendly organic solvent such as acetonitrile and isopropanol, as well as low pH eluents comprising trifluoroacetic acid or formic acid. The MAbPac™ RP Column comprises a phenyl substituted resin, is based on wide-pore 4 μm polymer spherical particles that are stable at extreme pH (0-14) and high temperature (up to) 110°, and has a pore size of 1,500 Å.

In one aspect of the invention, the reverse phase chromatography medium is coupled online with one or more additional chromatography media, such as an affinity chromatography medium, as described in detail herein. In another aspect, the chromatography media of the invention can be coupled directly to mass spectrometry (MS) using methods known to one of ordinary skill in the art.

IV. Antibodies for Use in the Methods of the Invention

The present invention provides the use of an online, two dimension liquid chromatography (2D-LC) method for the separating antibody variants comprising at least an Fc portion. In one aspect, one dimension is an affinity chromatography medium. In another aspect, the second dimension is a reverse phase chromatography medium.

In one aspect, "separating" includes one or more of: selecting purified antibody variants from parent/control antibodies or from other antibody variants, identifying and/or analyzing the presence of antibody variants in a sample, and assessing binding between antibody variants and FcRn as compared to a control antibody lacking modifications or variations. In one aspect, the online 2D-LC is coupled with mass spectrometry (MS).

In one aspect, the term "antibody" used in the methods of the invention includes a fusion polypeptide which comprises at least an FcRn binding portion of an Fc-region. For example, the fusion polypeptide can comprise an antibody fragment (e.g., a scFv molecule, a minibody, a tetravalent minibody, or a diabody) operably linked to an FcRn binding portion. In one aspect, the FcRn binding portion is a complete antibody heavy chain Fc-region.

Antibodies and antibody variants thereof can be contained in a sample for use in the methods of the invention.

In one aspect, the methods of the invention can be used to screen antibody variants of a control antibody which comprise at least an FcRn binding portion of an Fc-region for those modified antibodies that have an altered, e.g., increased or decreased, binding affinity for FcRn compared to the control antibody.

In another aspect, the methods of the invention can be used to purify antibody variants of a control antibody which comprise at least an FcRn binding portion of an Fc-region, from a sample containing control antibodies.

In another aspect, the methods of the invention can be used to identify and analyze the presence of antibody variants of a control antibody which comprise at least an FcRn binding portion of an Fc-region, from a sample containing control antibodies.

In certain aspects, antibodies assessed by the methods of the invention can include fusion polypeptides or modified fusion polypeptides which comprise at least an FcRn binding portion of an Fc-region.

In one aspect, the antibody is a monoclonal antibody. In one aspect the antibody is a chimeric antibody. In another aspect, the antibody is of an IgG1, IgG2, or IgG4 isotype.

In other aspects, an antibody used in the methods of the invention is a multispecific antibody, e.g., a bispecific antibody. Multispecific antibodies are monoclonal antibodies that have binding specificities for at least two different sites. In certain aspects, bispecific antibodies may bind to two different epitopes of the same antigen. Bispecific antibodies may also be used to localize cytotoxic agents to cells which express the antigen. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A., et al., EMBO J. 10 (1991) 3655-3659), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M., et al., Science 229 (1985) 81-83); using leucine zippers to produce bi-specific antibodies (see, e.g., Kostelny, S. A., et al., J. Immunol. 148 (1992) 1547-1553; using "diabody" technology for making bispecific antibody fragments (see, e.g., Holliger, P., et al., Proc. Natl. Acad. Sci. USA 90 (1993) 6444-6448); and using single-chain Fv (sFv) dimers (see, e.g. Gruber, M., et al., J. Immunol. 152 (1994) 5368-5374); and preparing trispecific antibodies as described, e.g., in Tuft, A., et al., J. Immunol. 147 (1991) 60-69).

Engineered antibodies with three or more functional antigen binding sites, including "Octopus antibodies," are also included herein (see, e.g. US 2006/0025576).

The antibody or fragment herein also includes a "Dual Acting Fab" or "DAF" comprising an antigen binding site that binds to different antigens (see, US 2008/0069820, for example).

The antibody or fragment herein also includes multispecific antibodies described in WO 2009/080251, WO 2009/080252, WO 2009/080253, WO 2009/080254, WO 2010/112193, WO 2010/115589, WO 2010/136172, WO 2010/145792, and WO 2010/145793.

In one aspect, the methods of the invention are used to purify, detect, identify and/or assess the FcRn binding of an antibody variant, including a PTM, including, but not limited to, antibody fragments, aggregates, acetylation variants, deamidation variants, oxidation variants, glycation variants, ubiquitination variants, glycosylation variants, charge variants, oligomerization variants, and antibodies with mutations in the Fc region of the antibody.

In certain aspects, the antibody variants are amino acid sequence variants. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In certain aspects, one or more amino acid modifications may be introduced into the Fc region of an antibody, thereby generating an Fc region antibody variant. The Fc region variant may comprise a human Fc region sequence (e.g., a human IgG1, IgG2, IgG3 or IgG4 Fc region) comprising an amino acid modification (e.g., a substitution) at one or more amino acid positions.

In certain aspects, the antibody variant may possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. FcRn binding and in vivo clearance/half-life determinations can also be performed using methods known in the art (see, e.g., Petkova, S. B., et al., Int. Immunol. 18 (2006) 1759-1769).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields, R. L., et al., J. Biol. Chem. 276 (2001) 6591-6604).

In certain aspects, an antibody variant comprises an Fc region with one or more amino acid substitutions which improve ADCC, e.g., substitutions at positions 298, 333, and/or 334 of the Fc region (Eu numbering of residues). In some aspects, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie, E. E., et al., J. Immunol. 164 (2000) 4178-4184.

Antibodies with increased half-lives and improved binding to the neonatal Fc receptor (FcRn), which is responsible for the transfer of maternal IgGs to the fetus (Guyer, R. L., et al., J. Immunol. 117 (1976) 587-593, and Kim, J. K., et al., J. Immunol. 24 (1994) 2429-2434), are described in US 2005/0014934. Those antibodies comprise an Fc region with one or more substitutions therein which improve binding of the Fc region to FcRn. Such Fc variants include those with substitutions at one or more of Fc region residues: 238, 252, 253, 254, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371, 826). See also Duncan, A. R. and Winter, G., Nature 322 (1988) 738-740; U.S. Pat. Nos. 5,648,260; 5,624,821; and WO 94/29351 concerning other examples of Fc region variants.

In certain aspects, an antibody variant used in the methods of the invention is a glycosylation variant. Where the antibody comprises an Fc region, the carbohydrate attached thereto may be altered. Native antibodies produced by mammalian cells typically comprise a branched, biantennary oligosaccharide that is generally attached by an N-linkage to Asn$^{297}$ of the CH2 domain of the Fc region. See, e.g., Wright, A. and Morrison, S. L., TIBTECH 15 (1997) 26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some aspects, modifications of the oligosaccharide in an antibody of the invention may be made in order to create antibody variants with certain improved properties.

In one aspect, antibody variants have a carbohydrate structure that lacks fucose attached (directly or indirectly) to an Fc region. For example, the amount of fucose in such antibody may be from 1% to 80%, from 1% to 65%, from 5% to 65% or from 20% to 40%. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki, A., et al., J. Mol. Biol. 336 (2004) 1239-1249; Yamane-Ohnuki, N., et al., Biotech. Bioeng. 87 (2004) 614-622.

Antibodies variants can also comprise bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc region can also be used in the methods of the invention. Such antibody variants are described, e.g., in WO 1997/30087; WO 1998/58964; and WO 1999/22764.

Antibody variants that can be used in the methods of the invention also include oxidation variants. Methionine oxidation is a very common PTM that can impact the bioactivity of the antibody and potentially induce an immunogenic response. Most IgG1 antibodies have two conserved heavy chain methionine residues located at the interface of the CH2 and CH3 domains. It has been reported that oxidation of these two methionine residues decreased thermal stability, protein A binding, FcRn binding and circulation half-life of IgG1 antibodies (Mo et al. Analytical Chemistry, 2016, 88, 9495-9502). Other amino acids (cysteine, histidine, tryptophan, and tyrosine) are also susceptible to oxidation. However, oxidation of antibodies outside of the Fc region will likely not effect antibody-FcRn binding.

The present invention is further illustrated by the following Examples, which is not intended to be limiting in any way. The entire contents of all references, patents and published patent applications cited throughout this application, as well as the Figures, are hereby incorporated herein by reference.

EXAMPLES

Example 1: Two Dimension Liquid Chromatography (2D-LC)-Mass Spectrometry (MS) Method In order to quickly assess the effect of antibody variants, including post-translational modifications (PTMs), on the binding between an antibody and the neonatal Fc Receptor (FcRn), an online, two dimension liquid chromatography (2D-LC)-mass spectrometry (MS) method has been developed.

Materials and Methods

FcRn Affinity Chromatography Column

The FcRn Affinity Column packed with 1 mL of FcRn-Biotin-Streptavidin-Sepharose resin, 34 µm, was purchased from Roche Custom Biotech (Mannheim, Germany; Cat. No. 08128057001). The FcRn column had a flow rate of 0.08 mL/min and was operated at 25° C. The column was prepared according to the manufacturer's instructions.

Samples comprising antibodies were diluted with buffer A (20 mM MES/HCL, pH 5.5, 140 mM NaCl) to a protein concentration of approximately 5 mg/mL. A sample volume of 2 µL (10 µg) was injected onto the column, which was equilibrated with 20 mM MES/HCl, 140 mM NaCl at pH 6.0.

Reverse Phase Chromatography Column

The reverse phase chromatography column was MAbPac-RP, 2.1 mm×50 mm, 4 µm (Thermo Fisher Scientific; Cat. No. 088648). The column was prepared according to the manufacturer's instructions. The reverse phase column had a flow rate of 0.3 mL/min and was heated at 80° C. for separation. The column was equilibrated with 0.1% formic acid, 1% acetonitrile in water. The online collected fractionations (40 µL) from affinity chromatography was sequentially injected on the column for desalting and further separation.

UV Detection

A Diode Array Detector (DAD) was used on the first and second dimension with the wavelength set at 280 nm.

Antibodies

Antibodies tested using the 2D-LC-mass spectrometry (MS) method included antibody number 1 (an IgG4 isotype monoclonal antibody); antibody number 2 (an IgG4 isotype, bispecific antibody); antibody number 3 (an IgG1 isotype antibody); and antibody number 4 (a bispecific IgG4 isotype antibody having a different sequence from antibody number 2).

Method Description

The 2D-LC-mass spectrometry (MS) method described herein was validated as follows.

Figure 3A:
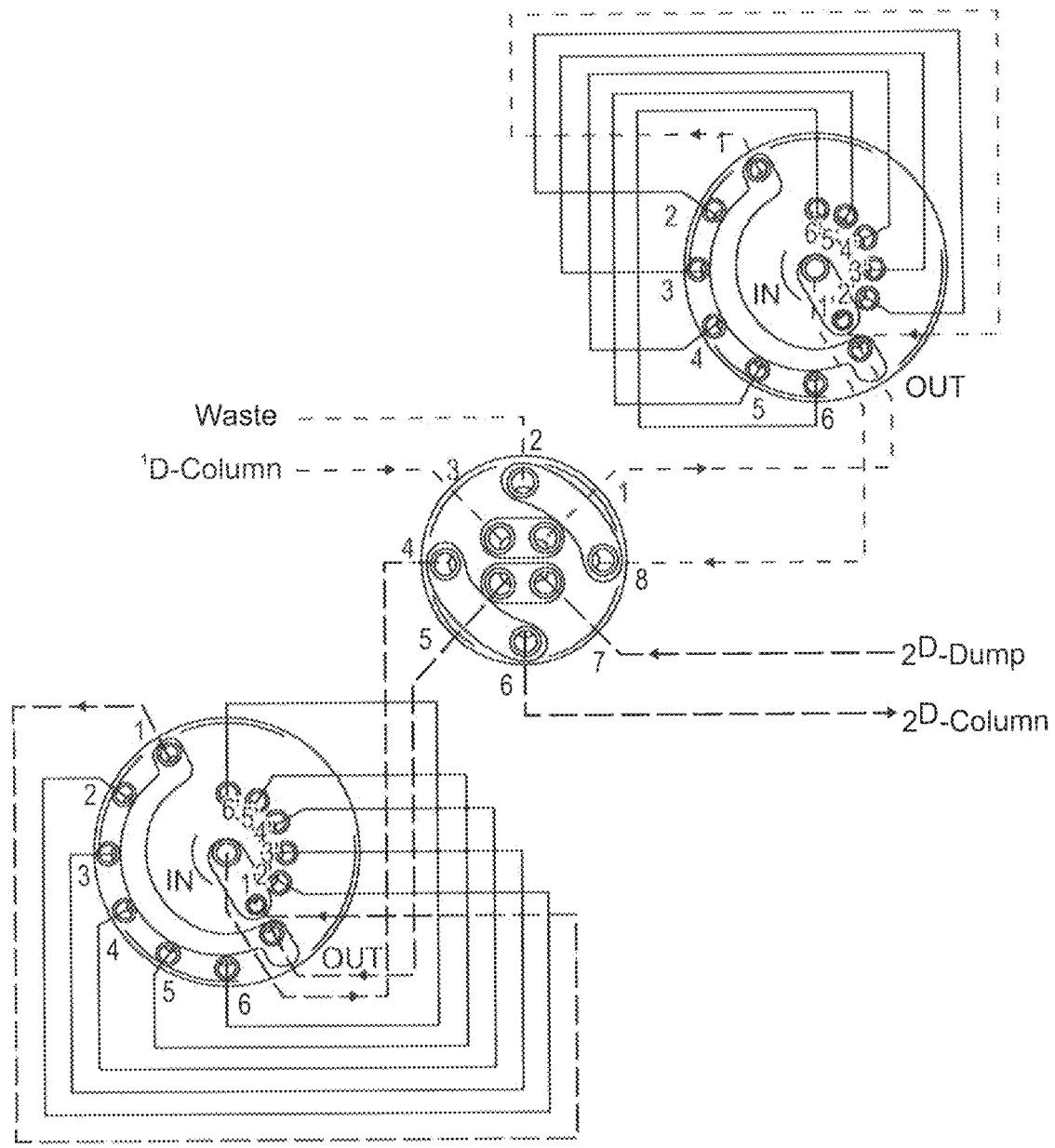
FIG. 3A depicts a 2D-LC valve connected with two 6-position/14 port selection valves.
Figure 3B:
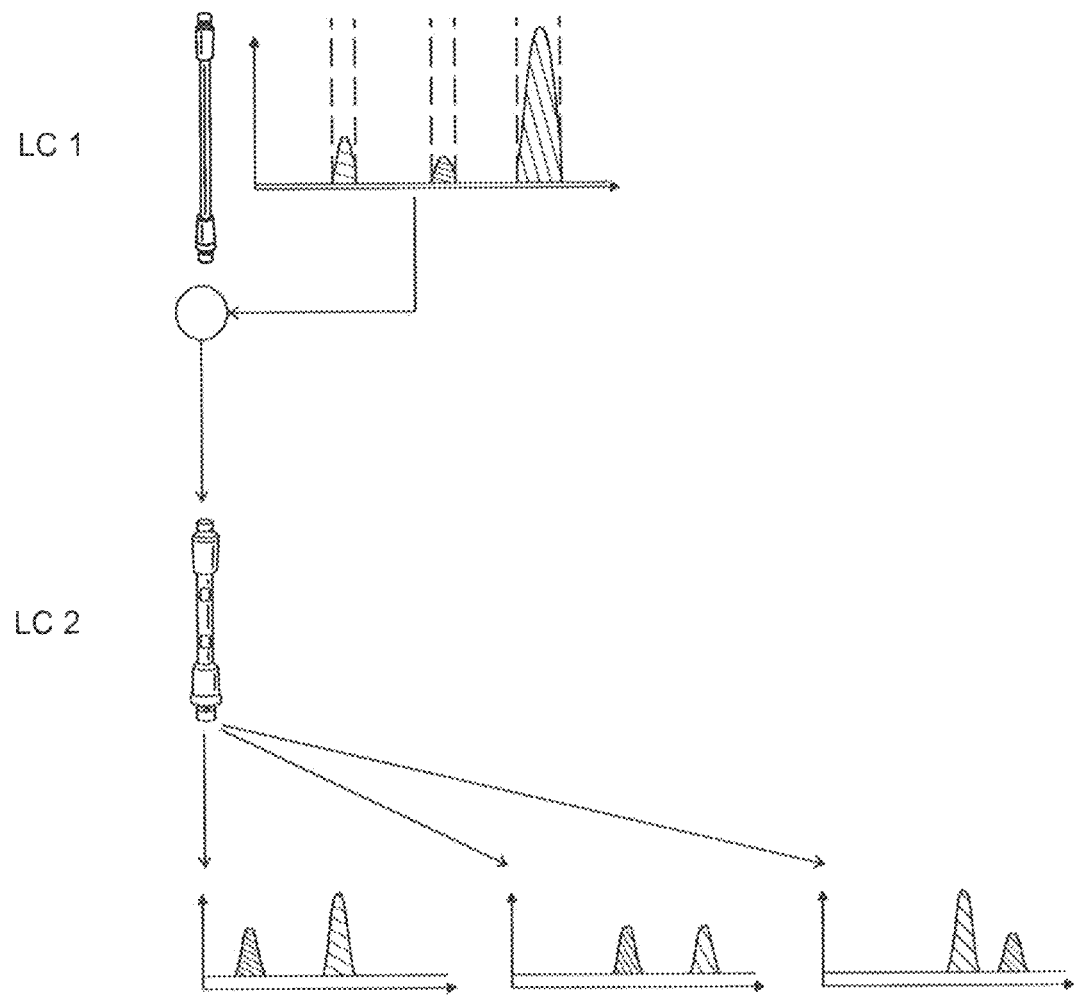
FIG. 3B depicts a 2D-LC valve connected with multiple heart-cutting 2D-LC.

FIG. 2A depicts the online 2D-LC-QE-HF-MS platform set-up and conditions used in this Example. Instruments utilized included a 1290 Infinity II™ UHPLC (Agilent Technologies) and a Q Exactive HF Hybrid (QE-HF) Quadrupole-Orbitrap™ Mass Spectrometer (Thermo Fisher Scientific) (see FIG. 2A). FIGS. 3A and 3B depict a 2D-LC valve connected with two 6-position/14 port selection valves (FIG. 3A) and multiple heart-cutting 2D-LC (FIG. 3B).

The first-dimension affinity separation was conducted on a stationary phase containing immobilized FcRn (Roche Diagnostics, Germany) using the buffers and conditions set forth in FIG. 2B (referred to as column 1). In particular, the sample was loaded in an acidic mobile phase using 80% buffer A (20 mM MES/HCl, pH 5.5, 140 mM NaCl) and 20% buffer B (20 mM Tris/HCl, pH 8.8, 140 mM).

Antibodies and antibody PTM variants bound to the FcRn affinity column were eluted from the column using a positive pH gradient, which mimics the physiological FcRn-IgG binding and dissociation process, using the buffers and conditions set forth in FIG. 2B.

The eluted antibody species of interest was sequentially fractionated, desalted and further separated online with the second-dimension reverse phase column using the buffers and conditions set forth in FIG. 2C (referred to as column 2). In particular, the sample was loaded in a 99% buffer A (0.1% formic acid in water) and 1% buffer B (0.1% formic acid in acetonitrile), and eluted over time as set forth in FIG. 2C.

The samples were then analyzed directly by MS.

Results

Figure 4:
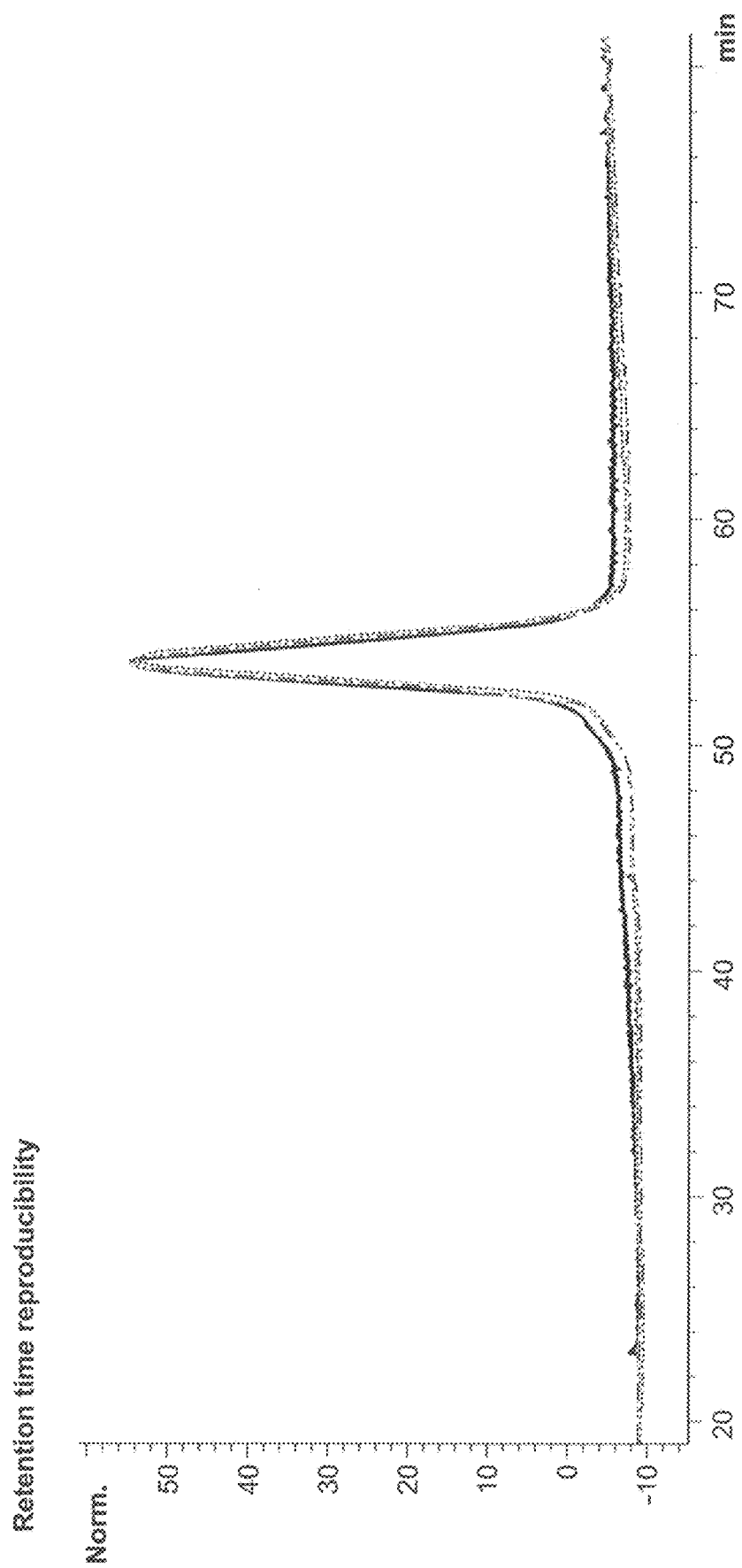
FIG. 4 depicts 1D UV chromatograms of antibody number 1, which was injected on day 1 (top line) and day 2 (lower two lines).

FIG. 4 depicts one dimension UV chromatograms of antibody number 1, which was injected on day 1 (blue) and day 2 (red and green).

Figure 5:
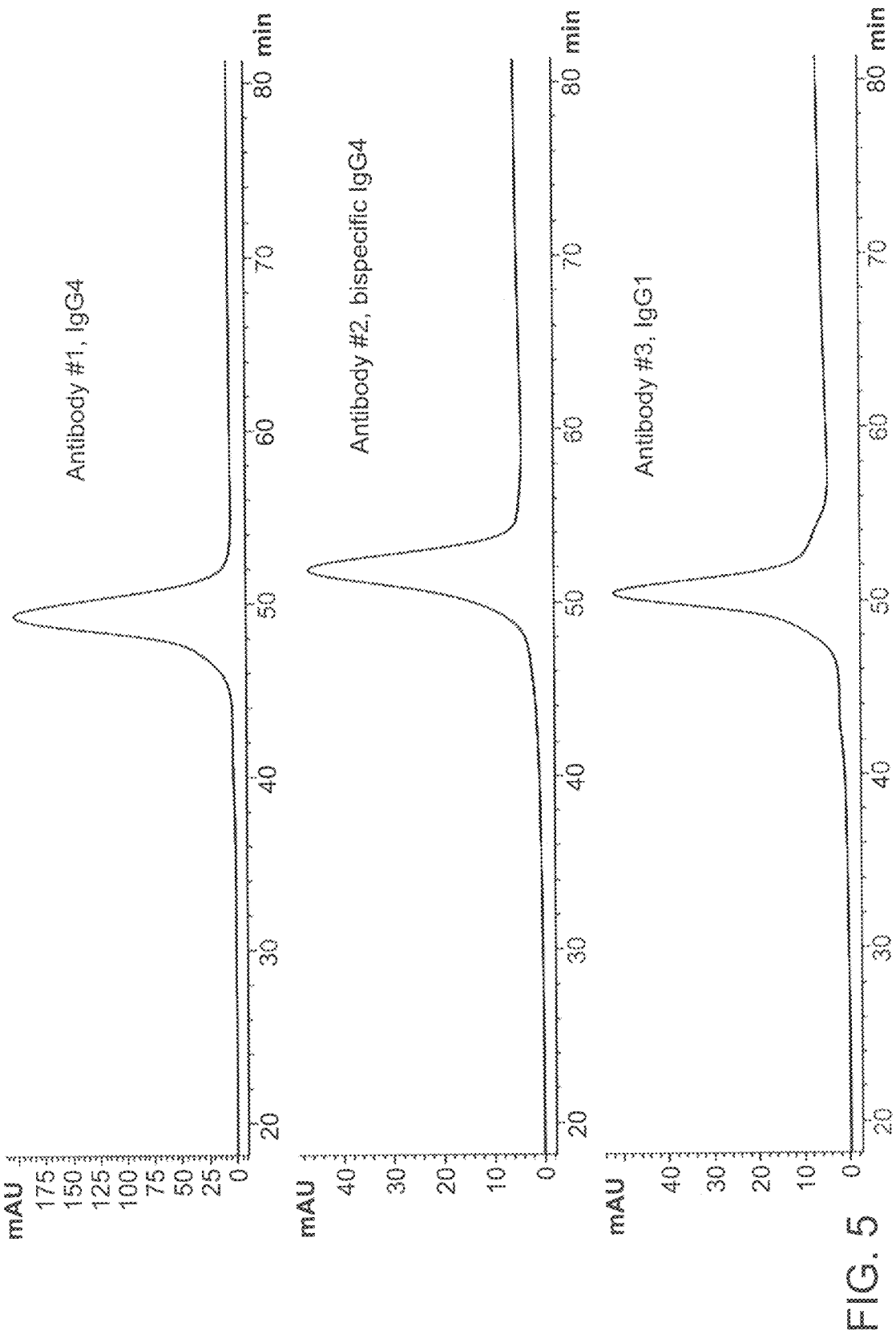
FIG. 5 depicts 1D UV chromatograms of three different types of antibodies (antibody number 1, IgG4 isotype; antibody number 2, IgG4 isotype, bispecific; and antibody number 3, IgG1 isotype).

FIG. 5 depicts one dimension UV chromatograms of antibody number 1 (an IgG4 isotype monoclonal antibody); antibody number 2 (an IgG4 isotype, bispecific antibody); and antibody number 3 (an IgG1 isotype antibody).

This FcRn 2D-LC-MS method can simultaneously evaluate FcRn-IgG binding, while identifying critical PTMs on the separated variants that can influence FcRn binding. Using this 2D-LC approach, sample handling is minimized, and potential contamination and sample loss are also reduced.

Example 2: Characterization and Evaluation of Antibody Oxidation and Deamidation Variants Using 2D-LC-Mass Spectrometry The online two dimension liquid chromatography (2D-LC)-mass spectrometry (MS) method as described in Example 1 has been successfully applied to characterize monoclonal antibodies and their oxidation variants. The method was applied to analyze the sample set including: (1) oxidative stressed antibody number 3, therein the antibody was incubated with 0.1% hydrogen peroxide ($H_2O_2$) at 37° C. for 12 hours (Table 1); (2) pH 9 treated antibody number 3, wherein the antibody was incubated in Tris buffer, pH 9 at 37° C. for 6 days (Table 2); and (3) native antibody number 3 as the control.

The intact mass analysis revealed the oxidation on intact antibody under oxidative stress condition and the deamidation as a result of pH 9 treatment of antibody. Further peptide mapping experiment confirmed that (1) almost complete oxidation at $Met^{78}$, $Met^{258}$ and $Met^{434}$ on oxidative stressed antibody number 3 (2) elevated level of deamidation at $Asn^{390}$ and $Asn^{395}$.

TABLE 1

Complete oxidation at $Met^{78}$, $Met^{258}$ and $Met^{434}$ on the oxidative stressed antibody number 3.

| | | Oxidation Percentage | |
|---|---|---|---|
| Chain | Site and Modification | Control Antibody | Oxidized Antibody |
| HC | $M^{78}$ sulfoxide | 2.75% | 100.00% |
| HC | $M^{78}$ sulfone | 0.00% | 0.40% |
| HC | $M^{258}$ sulfoxide | 4.11% | 99.80% |
| HC | $M^{258}$ sulfone | 0.01% | 1.27% |
| HC | $M^{434}$ sulfoxide | 0.01% | 100.00% |

TABLE 2

Deamidation profile of the pH 9 treated antibody number 3

| | | Deamidation Percentage | |
|---|---|---|---|
| Chain | Site and Modification | Control Antibody | pH Stressed Antibody |
| LC | $N^{53}$ | 0.02% | 0.08% |
| HC | $N^{331}$ | 0.40% | 0.22% |
| LC | $N^{158}$ | 0.09% | 0.27% |
| HC | $N^{321}$ | 0.10% | 0.35% |
| HC | $\sim N^{292}$ | 0.07% | 0.68% |
| HC | $N^{84}$ | 0.16% | 1.08% |
| HC | $\sim N^{59}$ | 0.35% | 1.88% |
| HC | $N^{303}$ | 0.42% | 2.12% |
| HC | $N^{390}$ | 1.96% | 16.85% |
| HC | $\sim N^{395}$ | 2.05% | 23.58% |

Results

Figure 6:
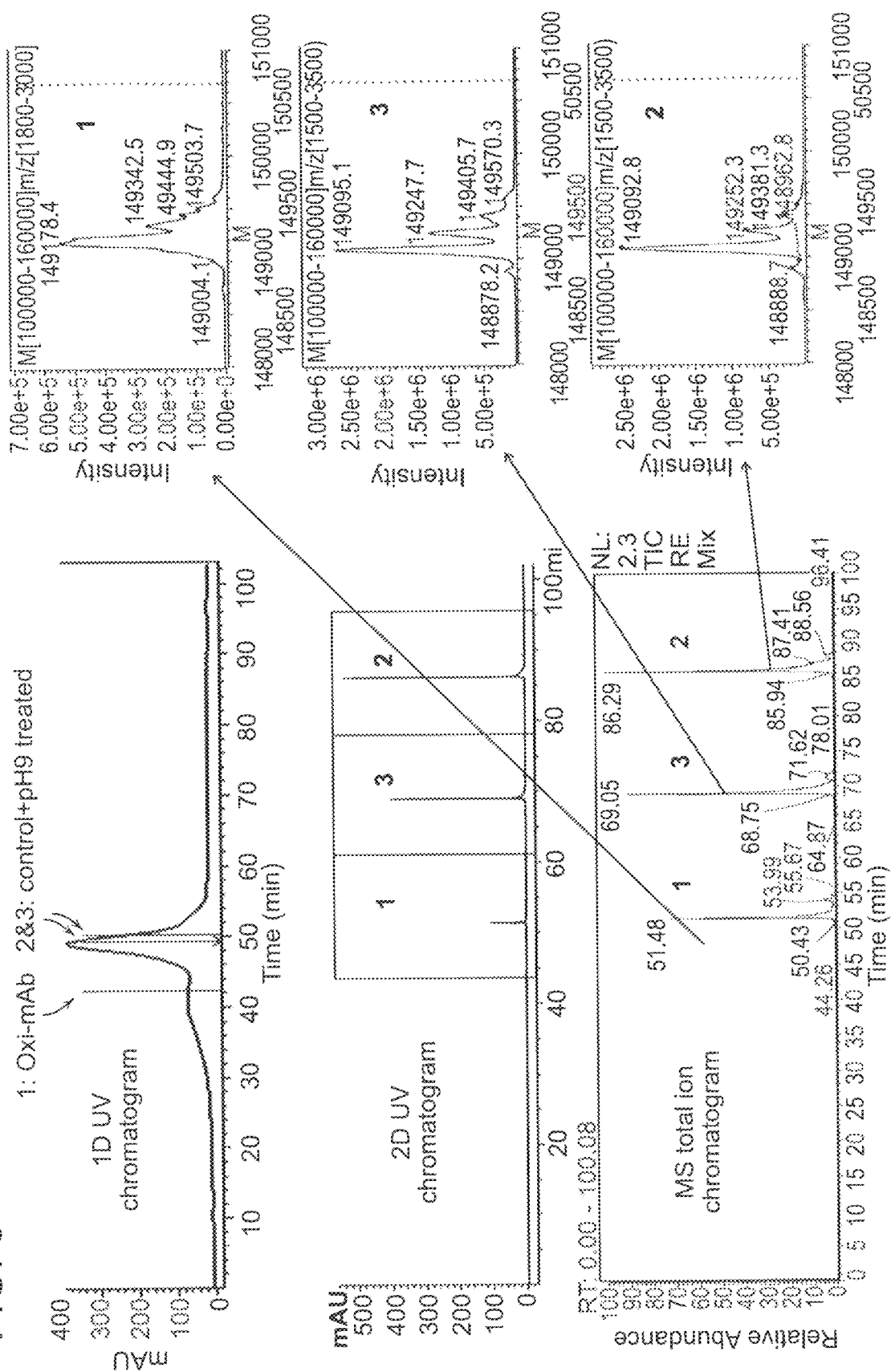
FIG. 6 depicts a 2D-LC chromatogram and mass spectra of the mixture of three antibody number three samples.

FIG. 6 depicts a two dimension chromatogram and mass spectra of the mixture of three antibody number 3 samples as described above. The oxidative stressed antibody number 3 eluted ahead of the control sample on FcRn column, indicating that the binding of the antibody number 3 to FcRn was significantly weakened by complete oxidation on $Met^{258}$ and $Met^{434}$. The binding site for FcRn is located at the interface between the CH2 and CH3 domains of human IgG. The structure changes associated with fully oxidized Met on CH2 domain was directly correlated to decreased binding affinity of mAb to FcRn. The antibody number 3 treated under high pH has the similar binding affinity to FcRn to the control, because $Asn^{390}$ and $Asn^{395}$ are not at the binding sites of IgG to FcRn.

Thus, compared to the native antibodies, decreased binding was observed for antibodies exhibiting high levels of oxidation. This result has been confirmed by Biacore™ assay.

SPR-Biacore™ Assay: Weak binding of antibody number 3 to human FcRn receptor was detected with KD in µM range. Decreased binding affinity was measured for oxidative stressed antibody number 3 to human FcRn, confirming the results from the FcRn affinity LC-MS assay (see Table 3).

TABLE 3

Dissociation constant (KD) measured by Biacore™ assay.

| Samples | hFcRn KD @ PBS buffer, pH 6.0 |
|---|---|
| Control antibody number 3 | 1.08 + .08 μM |
| Oxidative stressed antibody number 3 | 8.0 + 3.0 μM |

Example 3: Effect of Incubation Time on Oxidation Level of Antibody-FcRn Binding The online two dimension liquid chromatography (2D-LC)-mass spectrometry (MS) method as described in Example 1 has also been applied to investigate the effect of PTMs on antibody-FcRn binding for antibody number 4 stability study samples including: (1) T=0 control sample, (2) the antibody incubated for 28 days at 45° C., and (3) the antibody incubated for 57 days at 45° C.

Figure 7:
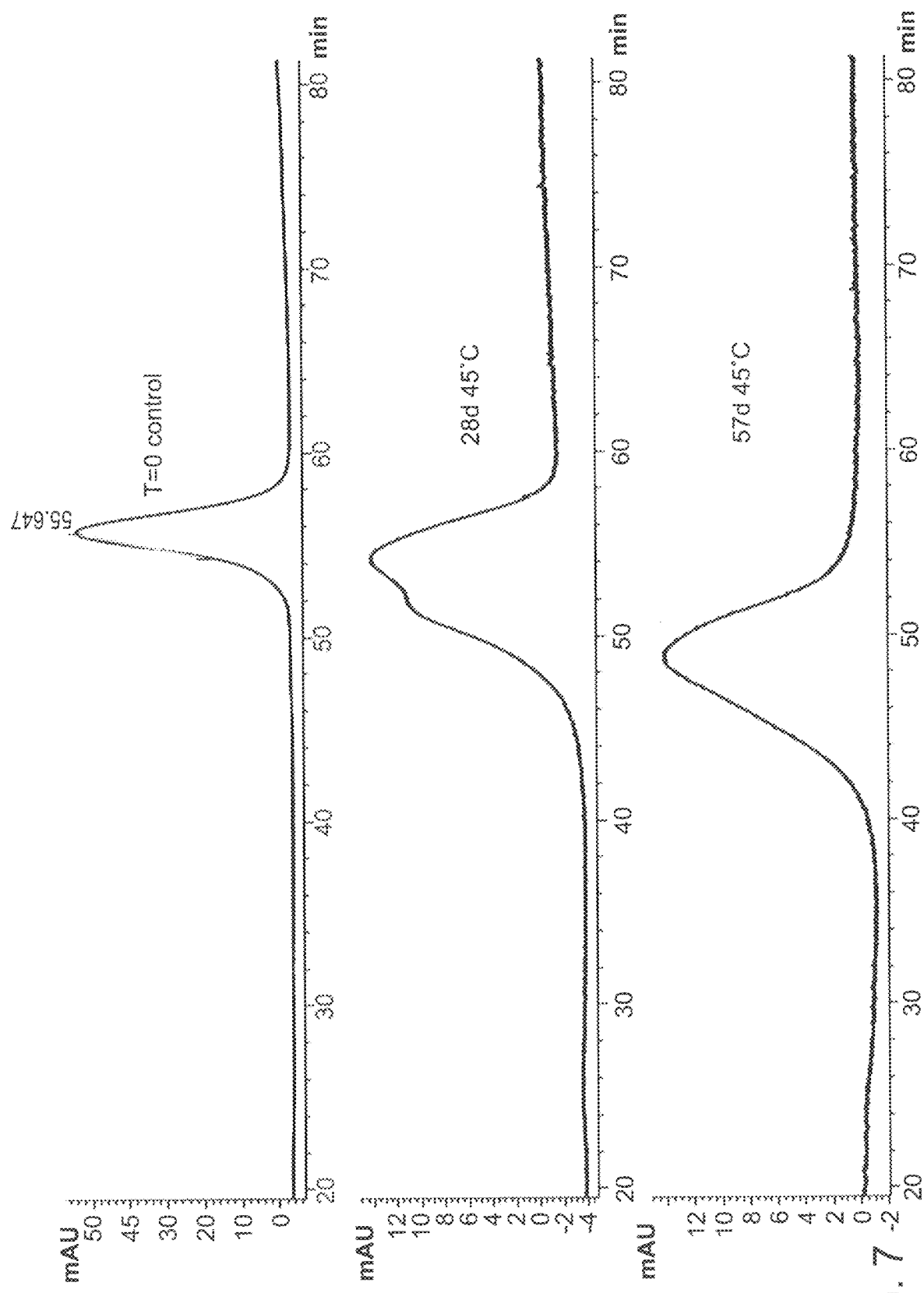
FIG. 7 depicts 1D UV chromatograms of antibody number 4 stability study samples. Antibody number 4 is a bispecific IgG4 isotype having a different sequence than antibody number 2.

As the incubation time increased, the oxidation level increased (see Table 4), and the antibody affinity to FcRn decreased, as shown in FIG. 7.

TABLE 4

Site location and percentage of oxidation of antibody number 4 stability study samples.

| | Oxidation Percentage | | |
|---|---|---|---|
| Site Location | T = 0 | 28 d 45° C. | 57 d 45° C. |
| HC Met$^{258}$/HC* Met$^{254}$ | 3.69% | 49.63% | 99.14% |
| HC Met$^{364}$/HC* Met$^{360}$ | 0.57% | 11.69% | 80.92% |
| HC* Met$^{430}$ | 0.63% | 20.79% | 81.19% |
| HC Met$^{434}$ | 1.03% | 19.33% | 91.83% |

Equivalents

Those skilled in the art will recognize, or be able to ascertain using no more than routine experimentation, many equivalents to the specific aspects of the invention described herein. Such equivalents are intended to be encompassed by the following claims. The contents of all references, patents and published patent applications cited throughout this application are incorporated herein by reference.

The invention claimed is:

1. A method for separating antibody variants or fragments thereof comprising at least a neonatal Fc receptor (FcRn) binding portion of an Fc-region and assessing binding affinity of the antibody variants or fragments thereof to the FcRn, using an online two dimension liquid chromatography system, the method comprising:
  a) contacting a first sample comprising antibody variants to an affinity chromatography stationary phase at an acidic pH and non-denaturing conditions, wherein the affinity chromatography stationary phase comprises immobilized FcRn or a fragment thereof, to thereby bind the antibody variants to the stationary phase;
  b) eluting the antibody variants from the affinity chromatography stationary phase using a positive pH gradient, to obtain an eluted sample;
  c) contacting the eluted sample to a reverse phase chromatography stationary phase; and
  d) eluting the reverse phase chromatography in a mobile phase to obtain a second eluted sample,
  wherein the reverse phase chromatography uses a mobile phase comprising a first buffer solution comprising 0.1% formic acid in water, and a second buffer solution comprising 0.1% formic acid in acetonitrile,
  wherein:
    i) an initial buffering solution for the reverse phase chromatography comprises about 99% of the first buffer solution and about 1% of the second buffer solution, and subsequently,
    ii) the first buffer solution is decreased to about 10% and the second buffer solution is increased to about 90% over time, and subsequently,
    iii) the first buffer solution is increased to about 99% and the second buffer solution is decreased to about 1%, and
  wherein antibody variants that elute ahead of a control sample are identified as having weaker binding affinity to FcRn than the control sample.

2. The method of claim 1, further comprising analyzing the second eluted sample using mass spectrometry (MS).

3. The method of claim 1, wherein the acidic pH is a pH of about 6.0 or less.

4. The method of claim 1, wherein the positive pH gradient comprises an increase in pH from about pH 6.0 to about pH 8.8.

5. The method of claim 1, wherein the sample is contacted to the affinity chromatography stationary phase in the presence of one or more buffer solutions.

6. The method of claim 5, wherein the one or more buffer solutions comprise 80% of a first buffer solution comprising 20 mM MES/HCl, pH 5.5, 140 mM NaCl and 20% of a second buffer solution comprising 20 mM Tris/HCl, 140 mM NaCl, pH 8.8 at pH 6.0.

7. The method of claim 1, wherein the pH gradient is generated using one or more buffer solutions.

8. The method of claim 7, wherein a first buffer solution comprises 20 mM MES/HCl, pH 5.5, 140 mM NaCl and a second buffer solution comprises 20 mM Tris/HCl, pH 8.8, 140 mM NaCl.

9. The method of claim 8, wherein the second buffer solution is increased from 20% to 100% to create the pH gradient.

10. The method of claim 1, wherein the pH gradient is a linear gradient.

11. The method of claim 1, wherein the pH gradient is a step gradient.

12. The method of claim 1, wherein the pH gradient mimics the physiological FcRn-IgG binding and dissociation process.

13. The method of claim 1, wherein the flow rate of the affinity chromatography is about 0.08 mL/min.

14. The method of claim 1, wherein the flow rate of the reverse phase chromatography is about 0.3 mL/min.

15. The method of claim 1, wherein the eluted sample is contacted to the reverse phase chromatography stationary phase in the presence of 0.1% formic acid in water (99%) and 0.1% formic acid in acetonitrile (1%).

16. The method of claim 1, wherein the eluting from the reverse phase chromatography results in desalting and/or the further separation of the antibody variants.

17. The method of claim 1, wherein the antibody is of an IgG1, IgG2, or IgG4 isotype.

18. The method of claim 17, wherein the antibody is a bispecific antibody of an IgG4 isotype.

19. The method of claim 1, wherein the antibody variants contain a post-translational modification (PTM) of the antibody.

20. The method of claim 1, wherein the antibody variants are selected from the group consisting of an oxidized antibody, an antibody aggregate, a deamidated antibody, a glycoslyated antibody, and antibody variants with Fc mutations.

21. A method for separating antibody variants or fragments thereof comprising at least a neonatal Fc receptor (FcRn) binding portion of an Fc-region and assessing binding of the antibody variants or fragments thereof to the FcRn, using an online two dimension liquid chromatography system, the method comprising:
   a) contacting a first sample comprising antibody variants to an affinity chromatography stationary phase at an acidic pH and non-denaturing conditions, wherein the affinity chromatography stationary phase comprises immobilized FcRn or a fragment thereof, to thereby bind the antibody variants to the stationary phase;
   b) eluting the antibody variants from the affinity chromatography stationary phase using a positive pH gradient, to obtain an eluted sample;
   c) contacting the eluted sample to a reverse phase chromatography stationary phase;
   d) eluting the reverse phase chromatography in a mobile phase to obtain a second eluted sample; and
   e) analyzing the second eluted sample using mass spectrometry (MS),
   wherein the reverse phase chromatography uses a mobile phase comprising a first buffer solution comprising 0.1% formic acid in water, and a second buffer solution comprising 0.1% formic acid in acetonitrile,
   wherein:
   i) an initial buffering solution for the reverse phase chromatography comprises about 99% of the first buffer solution and about 1% of the second buffer solution, and subsequently,
   ii) the first buffer solution is decreased to about 10% and the second buffer solution is increased to about 90% over time, and subsequently,
   iii) the first buffer solution is increased to about 99% and the second buffer solution is decreased to about 1%, and
   wherein antibody variants that elute ahead of a control sample are identified as having weaker binding to FcRn than the control sample.

22. The method of claim 1, wherein the control sample comprises a wild-type antibody or an antibody that does not contain the same variant as the variant antibodies being tested.

23. The method of claim 21, wherein the control sample comprises a wild-type antibody or an antibody that does not contain the same variant as the variant antibodies being tested.

* * * * *